(12) United States Patent
Kamii et al.

(10) Patent No.: US 8,432,660 B2
(45) Date of Patent: Apr. 30, 2013

(54) ION GENERATING UNIT AND LIGHTING APPARATUS

(75) Inventors: Miwa Kamii, Osaka (JP); Yasutaka Kataoka, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 73 days.

(21) Appl. No.: 13/056,859

(22) PCT Filed: Jul. 23, 2009

(86) PCT No.: PCT/JP2009/003454
§ 371 (c)(1),
(2), (4) Date: Jan. 31, 2011

(87) PCT Pub. No.: WO2010/013413
PCT Pub. Date: Feb. 4, 2010

(65) Prior Publication Data
US 2011/0128738 A1    Jun. 2, 2011

(30) Foreign Application Priority Data

Aug. 1, 2008   (JP) ................................. 2008-200139
Aug. 1, 2008   (JP) ................................. 2008-200141

(51) Int. Cl.
*H05F 3/00*   (2006.01)
*H01J 27/00*  (2006.01)

(52) U.S. Cl.
USPC ............ 361/230; 361/213; 361/231; 361/235

(58) Field of Classification Search .................. 361/230, 361/231, 213, 235
See application file for complete search history.

(56) References Cited

U.S. PATENT DOCUMENTS

| 7,586,731 | B2 * | 9/2009 | Sato et al. ..................... 361/231 |
| 7,649,728 | B2 | 1/2010 | Fujita et al. |
| 2005/0159795 | A1 * | 7/2005 | Savage et al. .................. 607/88 |
| 2006/0078460 | A1 * | 4/2006 | Ryu et al. .......................... 422/5 |
| 2008/0151465 | A1 | 6/2008 | Fujita et al. |

FOREIGN PATENT DOCUMENTS

| JP | 2001-19409 A | 1/2001 |
| JP | 2003-187945 A | 7/2003 |
| JP | 2004-55351 A | 2/2004 |
| JP | 2004-146335 A | 5/2004 |
| JP | 2005-155558 A | 6/2005 |
| JP | 2005-243288 A | 9/2005 |
| JP | 2007-216142 A | 8/2007 |
| JP | 2007-219010 A | 8/2007 |
| JP | 2007-227043 A | 9/2007 |
| JP | 2008159273 A | 7/2008 |
| JP | 2008-218372 A | 9/2008 |

* cited by examiner

*Primary Examiner* — Rexford Barnie
*Assistant Examiner* — Zeev V Kitov
(74) *Attorney, Agent, or Firm* — Birch, Stewart, Kolasch & Birch, LLP

(57) ABSTRACT

In an ion generating unit configured to control driving of a plurality of ion generating elements for generating ions by a controller, the controller drives the ion generating elements upon start up, and is configured to keep driving for a predetermined time period; thereby, the ion concentration of a space upon start up is quickly raised to a predetermined concentration. Further, the controller is configured to drive the ion generating elements intermittently and one after another in order after the predetermined time period has elapsed; the product life is elongated while maintaining the predetermined ion concentration and shortening the driving time of the ion generating elements.

15 Claims, 19 Drawing Sheets

F I G. 1 8

|  | FIRST BLUE LED | SECOND BLUE LED | GREEN LED | RED LED |
|---|---|---|---|---|
| ION GENERATING UNIT (HIGH MODE) | LIGHT | LIGHT | NON-LIGHT | NON-LIGHT |
| ION GENERATING UNIT (MEDIUM MODE) | NON-LIGHT | LIGHT | LIGHT | NON-LIGHT |
| ION GENERATING UNIT (LOW MODE) | NON-LIGHT | LIGHT | NON-LIGHT | NON-LIGHT |
| ION GENERATING UNIT (STOP) | NON-LIGHT | NON-LIGHT | NON-LIGHT | NON-LIGHT |
| DISPLAY OF REPLACEMENT TIMING OF FILTER | (SAME AS ABOVE OPERATION MODE) | | | LIGHT |
| DISPLAY OF REPLACEMENT TIMING OF ION GENERATING UNIT | NON-LIGHT | BLINK | BLINK | NON-LIGHT |

ION GENERATING UNIT AND LIGHTING APPARATUS

This application is the national phase under 35 U.S.C. §371 of PCT International Application No. PCT/JP2009/003454 which has an International filing date of Jul. 23, 2009 and designated the United States of America.

TECHNICAL FIELD

The present invention relates to an ion generating unit that generates ions by driving ion generator, and a lighting apparatus provided with the ion generating unit.

DESCRIPTION OF RELATED ART

In recent years, as a sealing property of internal spaces of buildings such as factories, offices and houses is improved, with an aim to realize a clean and comfortable working space or accommodation space, a desire to clean air by removing floating particles that are harmful to human body is ever growing. As a technique for such an air cleaning, conventionally, a technique of taking air within a target space, letting the air pass through a filter, and removing the floating particles by catching them with the filter had been widely adapted.

In an apparatus using such a filter, it is difficult to provide a cleaning effect to an entirety of the working space or accommodation space. For example, a sufficient cleaning effect cannot be expected in locations within a room where air tends to stagnate, such as behind a furniture arranged within a room and corners of the room. Further, there has been a problem that a sufficient removing effect cannot be achieved against harmful floating particles such as germs, viruses. To deal with this, in recent years, an apparatus using a technique that generates positive ions and minus ions from water within the air by an electric discharge to enclose and destroy the harmful floating particles such as germs, viruses floating in the air is being put into practice.

In the apparatus as above, in which particles such as ions to sterilize or disinfect the harmful floating particles such as germs, viruses are generated by the electric discharge, there is a desire to keep wear of components such as an electric discharge electrode at low level and elongate a product life of the apparatus. Various proposals therefor are being made (e.g., see Japanese Patent Application Laid-Open No. 2001-19409).

A high-pressure ozone generating apparatus disclosed in Japanese Patent Application Laid-Open No. 2001-19409 is configured to divide an electric discharge electrode pair into a plurality of blocks, alternately apply high voltage pulse voltage to the plurality of blocks to generate the electric discharge, and thereby generate an ozone. From this configuration, a transient state at the beginning of the discharge is used in improving an ozone generation efficiency and reducing an unnecessary wear of the electrodes, thereby achieving the elongation of product life.

SUMMARY

However, the high pressure ozone generating Japanese Patent Application Laid-Open No. 2001-19409 is configured such that a voltage is applied alternately to the electric discharge electrode pairs of the plurality of blocks to discharge the electricity, and then to generate the ozone, thus, compared to a case in which both of the electric discharge electrode pairs are used, there was a problem that upon start up of the apparatus, a long time is required until the ozone is filled in a space and reaches a predetermined concentration.

The present invention has been made in view of the above circumstances, and aims to provide an ion generating unit and a lighting apparatus including the ion generating unit, which are capable of quickly raising the ion concentration in a space to a predetermined concentration, and elongating a product life while maintaining the predetermined concentration.

An ion generating unit according to the present invention includes a plurality of ion generators configured to generate ions and a controller configured to control drive of the plurality of ion generators. Upon a start-up of the controller, the controller drives the plurality of ion generators, and after a predetermined time period has elapsed, the controller controls the plurality of ion generators to be driven such that a driving time of the plurality of ion generators is substantially equalized.

In the present invention, since the ion generating unit is configured to drive the plurality of ion generators upon its start-up, and drive the same over the predetermined time period, the ion concentration in the space upon start up can quickly be raised to the predetermined concentration. Further, since the plurality of ion generators are driven such that the driving time of the plurality of ion generators is substantially equalized after the predetermined time period has elapsed, a timing of replacing the plurality of ion generators can be synchronized, and a period during which the predetermined ion concentration can be maintained in the ion generating unit as a whole can be elongated. Consequently, the elongation of a product life can be achieved.

An ion generating unit according to the present invention includes a plurality of ion generators configured to generate ions and a controller configured to control drive of the plurality of ion generators. The controller selects and controls one of a first drive for driving the plurality of ion generators, and a second drive for driving the plurality of ion generators such that a driving time of the plurality of ion generators is substantially equalized.

In the present invention, the first drive and the second drive are configured to be selected and controlled. In accordance with a condition of usage of a room, one of the two drives can be selected. Thereby, the ion concentration in the space can be maintained at an appropriate concentration, the ion generators can be driven without any futility, and the elongation of a product life can be achieved.

In the ion generating unit according to the present invention, the controller controls to drive the plurality of ion generators one after another in order such that the driving time of the plurality of ion generators is substantially equalized.

In the present invention, since the plurality of ion generators are driven one after another in order, loads applied to the plurality of ion generators can be equalized. Wear of components such as the electric discharge electrodes that constitute the ion generators can be suppressed, and the elongation of a product life can be achieved.

In the ion generating unit according to the present invention, the controller controls to drive the plurality of ion generators one after another in order by driving respective ones of the plurality of ion generators intermittently.

In the present invention, the plurality of ion generators are configured to be driven intermittently, and the plurality of ion generators are further configured to be driven one after another in order; and since it takes some time for the generated ions to disappear, by shortening the driving time of the ion generators while maintaining the predetermined ion concentration, the wear of the components such as the electric discharge electrodes that constitute the ion generators, and the elongation of a product life can be achieved.

In the ion generating unit according to the present invention, the controller is configured so as to selectively drive the plurality of ion generators continuously.

In the present invention, the drive of the aforementioned invention and the drive of driving the plurality of ion generators continuously are configured to be capable of being selected, and thus it becomes possible to select the continuous drive in accordance with the condition of the usage of the room or the like. Thereby, the ion concentration in the space can be maintained at the appropriate concentration, the ion generators can be driven without any futility, and the elongation of a product life can be achieved.

A lighting apparatus according to the present invention includes a light source and an ion generating unit according to any one of the inventions described above.

In the present invention, a lighting apparatus in which an ion generating unit with long product life is integrated can be provided.

A lighting apparatus according to the present invention includes a light source and an ion generating unit according to any one of the inventions described above. The controller is configured to drive the plurality of ion generators in response to a turn-on of the light source.

In the present invention, the plurality of ion generators of the ion generating unit are configured to be driven in response to the light source of the lighting apparatus being turned on. Especially, in offices and factories, the lighting apparatus is typically turned on when a room is being used, therefore, the ion concentration of the room can quickly be raised to the predetermined concentration when a man uses the room, thereby a clean and comfortable working space or accommodation space can be realized, the ion generators can be driven without any futility, and the elongation of a product life can be achieved.

A lighting apparatus according to the present invention includes a light source and an ion generating unit according to any one of the inventions described above. The controller is configured to drive the plurality of ion generators such that an amount of generated ion becomes large/small in response to a turn-on/turn-off of the light source and/or high/low of illuminance thereof.

In the present invention, the amount of generated ion is configured to become large/small in response to the turn-on/turn-off of the light source and/or the high/low of the illuminance. Typically, the turn-on/turn-off of the light source and the high/low of the illuminance often correspond to a presence/absence of a man and a degree of activeness in human activities. Thus, a clean and comfortable working space or accommodation space can be realized, the ion generators can be driven without any futility, and the elongation of a product life can be achieved.

In the lighting apparatus according to the present invention, the light source is an LED.

In the present invention, the LED is used as the light source. The LED has a long product life, and by driving the ion generators according to the above described invention, a product life of the ion generators can be elongated; thus the number of replacing the ion generators or the light source can be reduced, and a trouble of the user can be saved.

According to the present invention, the ion concentration in the space can quickly be raised to the predetermined concentration upon start up, and the elongation of a product life of the ion generators can be achieved while maintaining the predetermined ion concentration.

The above and further objects and features will more fully be apparent from the following detailed description with accompanying drawings.

BRIEF DESCRIPTION OF THE SEVERAL VIEWS OF THE DRAWINGS

FIG. 18 is a table explaining lighting states of display LEDs in a display unit for displaying indications of operational states of the ion generating unit and indications of replacement timings of the filter and ion generating unit of FIG. 1.

DETAILED DESCRIPTION

Figure 1:
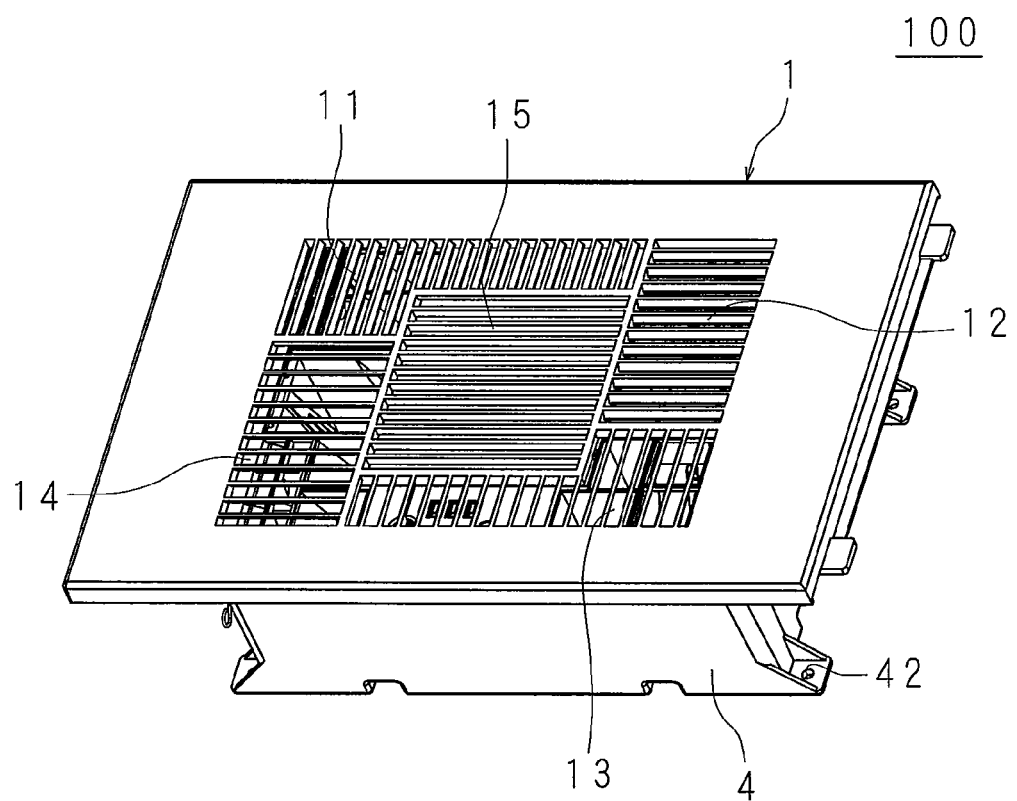
FIG. 1 is an external perspective view of an ion generating unit of the present invention.
Figure 2:
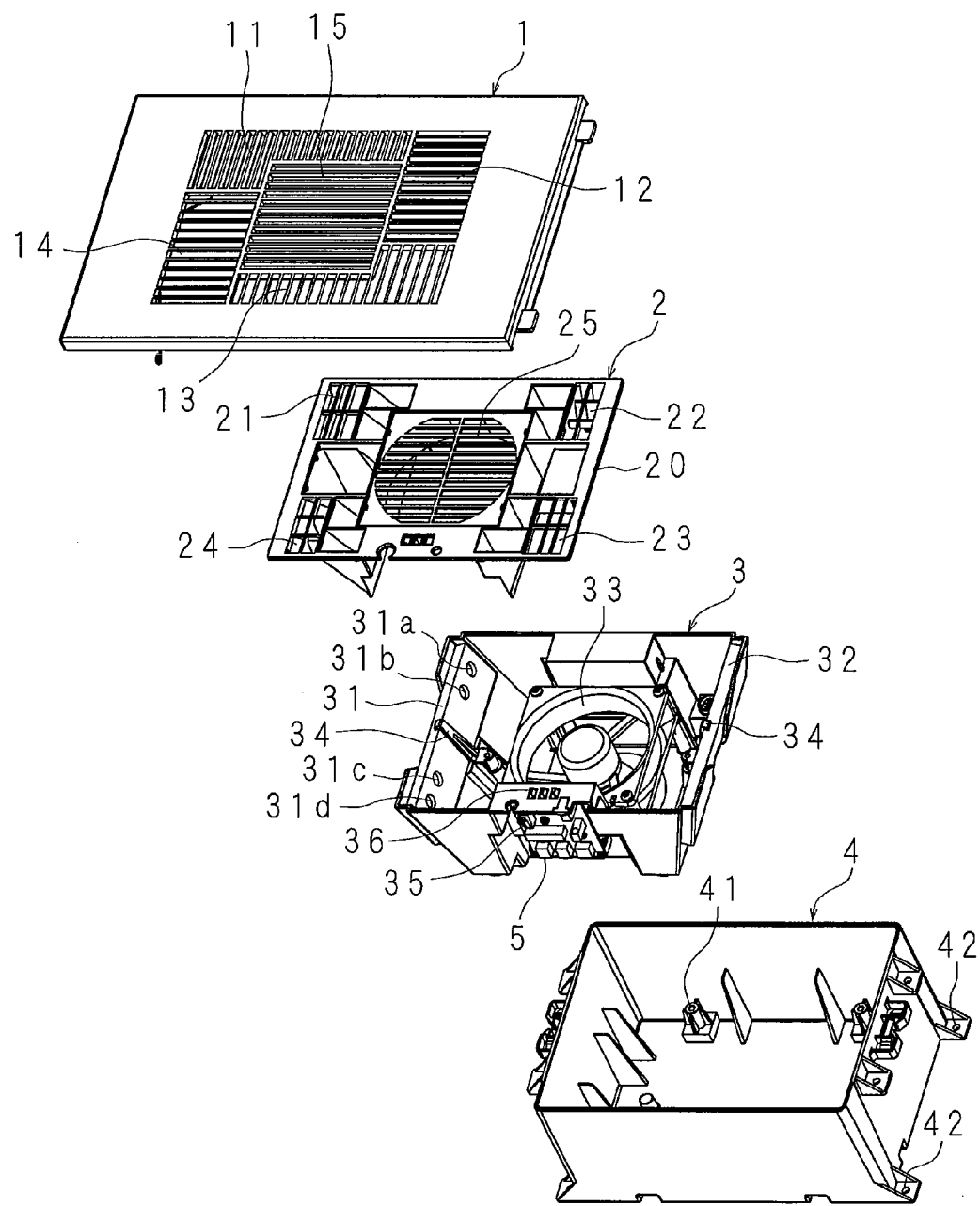
FIG. 2 is an exploded perspective view of the ion generating unit.
Figure 3:
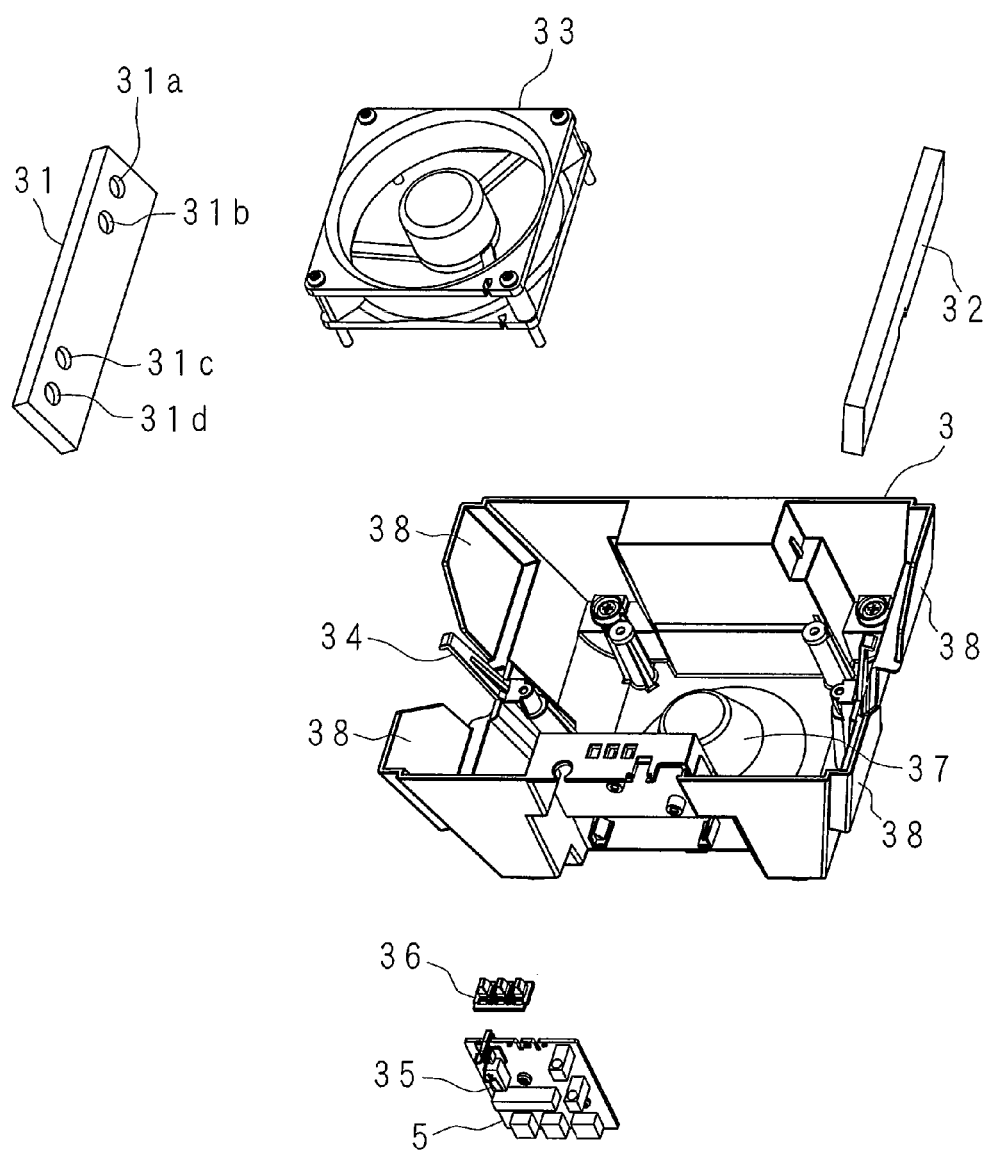
FIG. 3 is an exploded perspective view of a primary part of the ion generating unit.
Figure 4:
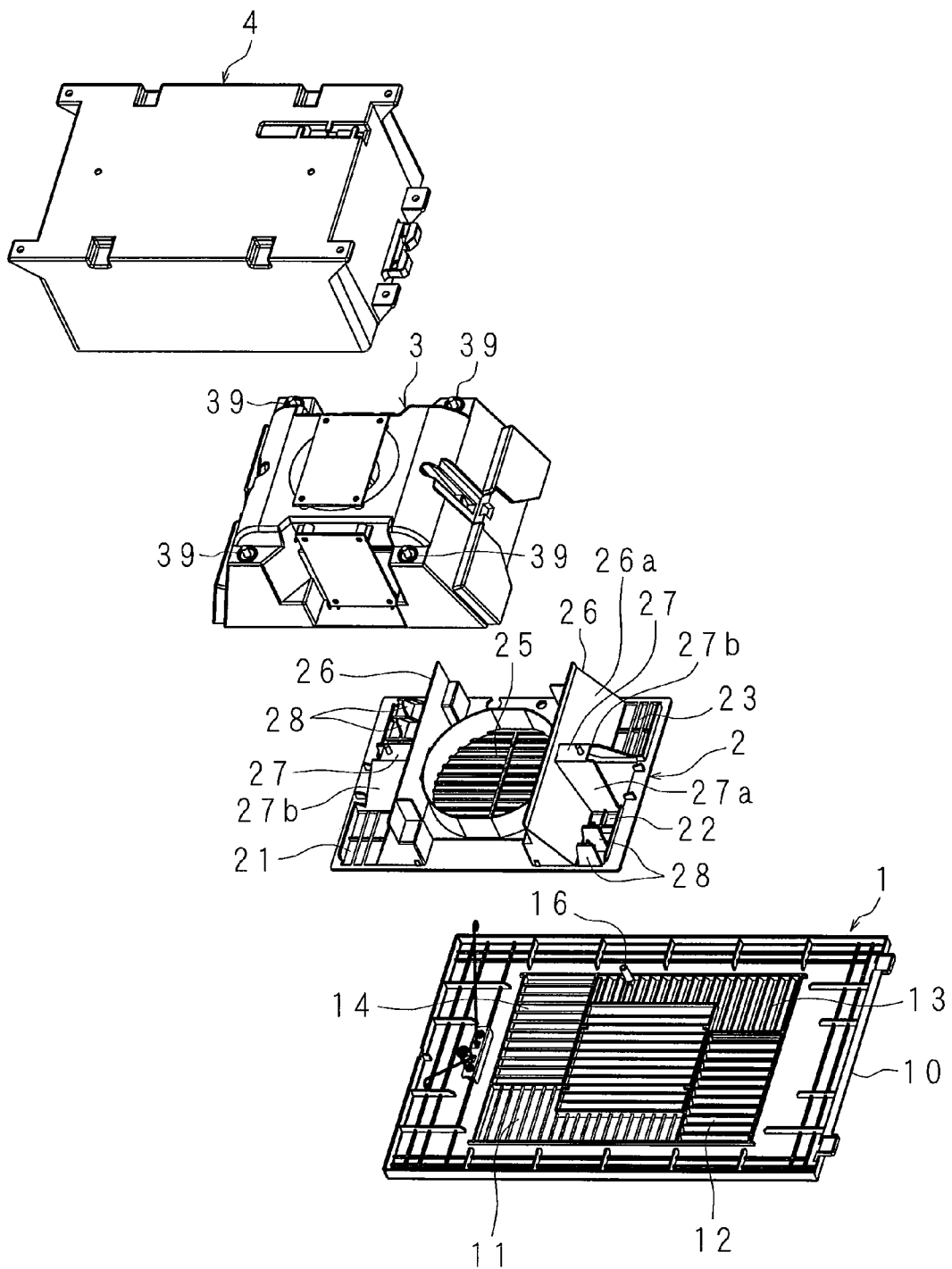
FIG. 4 is an exploded perspective view of the ion generating unit seen from a rear side.

Hereinbelow, the present invention will be described in detail with reference to the drawings showing embodiments thereof, using an example of an air cleaning unit provided with a fan for ventilating ions generated in ion generators serving as an ion generating unit. FIG. 1 is an external perspective view of an ion generating unit 100 of the present invention. FIG. 2 is an exploded perspective view of the ion generating unit 100. FIG. 3 is an exploded perspective view of a primary part of the ion generating unit 100. FIG. 4 is an exploded perspective view of the ion generating unit 100 seen from a rear side. It should be noted that in the description of the embodiments, a "front side" refers to a face on a side where an air outlet from which the ion containing air is blown out is provided, and a "rear side" refers to a face that is opposite the front side.

The ion generating unit 100 includes a substantially cuboid casing 4, a main body base 3 that is attached to an inside of the casing 4 and provided with an ion generating element A 31, an ion generating element B 32 and an axial stream fan 33 (hereinbelow referred to as a fan 33), an intake grill 2 that is attached to the main body base 3 and forms an air passage together with the main body base 3 for air taken in from outside, and a front side cover 1 (hereinbelow referred to as a cover 1) that is formed at a front side of the casing 4 and covers the main body base 3 and the intake grill 2.

The casing 4 has a box shape with one opened face, and is made of a synthetic resin such as plastic. The casing 4 is configured to be capable of attaching the main body base 3 to the inside of the casing 4 and housing the same therein by engaging attachment protrusions 39 (described later in detail) formed at a rear face of the main body base 3 with a plurality of attachment holes 41 formed at a bottom face of the casing 4. Further, at four corners of the casing 4, screw holes 42 for screw fixing to a bottom face of a housing of a lighting apparatus (described later in detail) are formed respectively.

The main body base 3 has a box shape with one opened face, with a size that is one size smaller than the casing 4, and is made of a synthetic resin such as plastic. The main body base 3 includes a set of side walls 38 facing each other, and this set of side walls 38 facing each other is angled at substantially 45° with respect to a bottom face of the main body base 3, such that the opened side becomes wider. At inner faces of these side walls 38, the ion generating element A 31 and the ion generating element B 32 as ion generators having rectangle plate shapes and generating ions are removably attached with fixing plates 34, 34, respectively. Specifically, the ion generating element A 31 and the ion generating element B 32 are fixed by being pressed against inclined surfaces, which are the inner faces of the side walls 38, by the fixing plates 34 to which latching portions are formed at the distal end thereof, respectively. On the other hand, by releasing the fixing plates 34, the ion generating element A 31 and the ion generating element B 32 can be removed.

The ion generating element A 31 includes a needle electrode as an electric discharge electrode and a plate electrode as an induction electrode, and the electric discharge electrode is arranged at an inside of a through hole formed in the induction electrode coaxially with the through hole; and is configured to discharge the electricity by applying a high voltage between the electric discharge electrode and the induction electrode. On one end side of the ion generating element A 31, minus ion generating electrode sections 31a, 31b for generating minus ions by the electric discharge are arranged at a suitable distance apart, and on another end side thereof, positive ion generating electrode sections 31c, 31d for generating positive ions by the electric discharge are arranged at a suitable distance apart. In a state where the ion generating element A 31 is attached to the inner faces of the side walls 38, it is configured such that in the vicinity of an outlet 21 and an air outlet 11, the minus ion generating electrode sections 31a, 31b for generating the minus ions are arranged; and, in the vicinity of an outlet 24 and an air outlet 14, the positive ion generating electrode sections 31c, 31d for generating the positive ions are arranged.

The ion generating element B 32 includes a similar configuration as the ion generating element A 31. Note that, the ion generating element B 32 is attached to the main body base 3 such that its positive ion generating electrode sections are arranged to face the minus ion generating electrode sections 31a, 31b of the ion generating element A 31, and its minus ion generating electrode sections are arranged to face the positive ion generating electrode sections 31c, 31d of the ion generating element A 31, respectively. In other words, in a state where the ion generating element B 32 is attached to inclined surfaces, which are the inner faces of the side walls 38, in the vicinity of an air outlet 12 and an outlet 22, the positive ion generating electrode sections for generating the positive ions are arranged, and, in the vicinity of an air outlet 13 and an outlet 23, the minus ion generating electrode sections for generating the minus ions are arranged. As mentioned above, the ion generating element A 31 and the ion generating element B 32 are each arranged such that their positive ion generating electrode sections and minus ion generating electrode sections are positioned diagonally; therefore, the positive ions and minus ions can be emitted in a well-balanced manner to external air.

These ion generating element A 31 and ion generating element B 32 generate $H^+(H_2O)_m$ (m is a voluntary natural number) as the positive ions and $O_2^-(H_2O)_n$ (n is a voluntary natural number) as the minus ions by ionizing water within the air by the electric discharge. Further, the generated $H^+(H_2O)_m$ and $O_2^-(H_2O)_n$ adhere to the floating germs and floating viruses and the like in the air, and by chemical reactions thereof, hydrogen peroxide ($H_2O_2$) and/or hydroxyl radical (OH), which are active species, are generated. $H_2O_2$ and/or OH exhibit extremely strong activation, and thus the floating germs and floating viruses and the like can be enclosed and removed thereby.

Further, as shown in FIG. 3, at a substantial center of the bottom face of the main body base 3, a semispherical tapered member 37 protruding forward is formed. The tapered member 37 is formed in a shape of a bowl which circularly tapers from an outside toward an inside, such that air taken in from an air intake (described later in detail) flows smoothly without much turbulence in air current thereof and is directed to an air outlet. The fan 33 having a plurality of wings such that its rotation axis forms a substantially orthogonal angle with the bottom face is attached to the tapered member 37.

By driving the fan 33, the air taken in to the inside of the main body base 3 via an air intake 15 of the cover 1 and an intake 25 of the intake grill 2 is blown toward the tapered member 37. The blown air can be flown smoothly in a direction of the side walls 38 from the bottom face of the main body base 3 due to the protruding shape of the tapered member 37. Further, since the side walls 38 are inclined, the air that has reached the side walls 38 can be flown smoothly in a direction of the front face of the main body base 3 along the inclinations of the side walls 38. That is, the protruding shape of the tapered member 37 and the inclined shapes of the side walls 38 of the main body base 3 have an effect of flowing the air smoothly, and the tapered member 37 and side walls 38 function as a rectifier.

Further, the main body base 3 is provided with an electrical circuit substrate 5 attached to one side wall of the main body base 3. The electrical circuit substrate 5 includes a microcomputer (hereinbelow referred to as microcomputer) for controlling the ion generating unit 100, a power circuit for generating a predetermined voltage to be supplied to the ion generating element A 31, the ion generating element B 32 and the fan 33, and a driving circuit for driving the ion generating element A 31, the ion generating element B 32 and the fan 33, and the like. Further, the main body base 3 is provided with a microswitch 35 for detecting an opened/closed state of the cover 1.

Further, the main body base 3 is provided with a display unit 36 including LEDs. The display unit 36 is configured to indicate operational states of the ion generating unit 100 by lighting states of the LEDs. Further, at the rear face of the main body base 3, the aforementioned attachment protrusions 39 that engage with the plurality of attachment holes 41 formed on the bottom face of the casing 4 are provided.

This main body base 3 is attached to the inside of the casing 4 such that a direction of its opened side coincides with that of the casing 4. At the opened side of the main body base 3 attached to the casing 4, the intake grill 2 is provided.

The intake grill 2 includes a plate 20 having a substantially identical dimension as the opened portion of the main body base 3, and an outlet direction setting member provided on one surface of the plate 20. At a substantial center of the plate 20 of the intake grill 2, the intake 25 is provided. At four corners of the plate 20 of the intake grill 2, the first outlet 21, the second outlet 22, the third outlet 23 and the fourth outlet 24 are provided. As shown in FIG. 4, in the intake grill 2, two passage walls 26 having inclined surfaces 26a that constitute the air passage together with the bottom face and the side faces of the main body base 3 for the air taken in from outside are provided on the rear face side facing the main body base 3, with the intake 25 interposed therebetween. Heights of the passage walls 26 are set to be lower than a depth of the main body base 3, and by making inclination angles of the inclined surfaces 26a of the passage walls 26 to be substantially identical to the inclination angles of the side walls 38(45° of the main body base 3, the air passage can be secured between the passage walls 26, bottom face of the main body base 3, and inner faces of the side walls 38.

Further, at a center of each of the passage walls 26, a passage plate 27 that function as a partition plate, in a state where the ion generating element A 31 and the ion generating element B32 are attached, for preventing the positive ions and minus ions from bonding is provided. The passage plate 27 has inclined surfaces 27a, 27b, and is capable of smoothly ventilating the air which has collided with the tapered member 37 of the main body base 3 and flows therefrom by dispersing the air to the respective outlets. The outlets 22, 24 that are arranged at diagonal positions include rectifying plates 28, and are capable of blowing air out toward directions different from those of the other outlets 21, 23. Thus, since the air blown out from the outlets 21, 22, 23, 24 are all directed to different directions, the positive ions and minus ions can be distributed with a favorable balance.

Accordingly, the passage walls 26, the passage plates 27 and the rectifying plates 28 constitute parts of the air passage, and further have a function as the outlet direction setting member that sets a direction toward which the air is blown out.

This intake grill 2 is attached to the main body base 3 such that the side of the plate 20 comes to be at the opened side of the main body base 3. Note that, the outlet direction setting member is configured to constitute the air passage which guides the air taken in by the fan 33 to the respective first outlet 21, second outlet 22, third outlet 23 and fourth outlet 24 in the state where the intake grill 2 is attached to the main body base 3.

On the opened side of the main body base 3, the cover 1, which is a guiding plate for the air flowing in and out of the ion generating unit 100, is attached thereto such that the plate 20 of the intake grill 2 is covered (the main body base 3 and intake grill 2 are covered from the front face side).

At the substantial center of the cover 1 at a position corresponding to the intake 25, the air intake 15 for taking in the external air into the inside of the main body base 3 is provided. At an outer periphery of the air intake 15 of the cover 1, at positions that respectively correspond to the first outlet 21, second outlet 22, third outlet 23 and fourth outlet 24 that surround the air intake 15, the first air outlet 11, second air outlet 12, third air outlet 13 and fourth air outlet 14 that blows out air containing ions generated from the ion generating element are provided.

Further, the outlets 21, 22, 23, 24 include slits constituted of a plurality of partition plates inclined along a blow-out direction toward which the air is blown out. By configuring the partition plates to be inclined in the blow-out direction, in addition to the aforementioned outlet direction setting member of the intake grill 2, the blow-out direction can be determined more accurately. Consequently, since the ion containing air can be distributed in all different directions, the floating germs and viruses in the room can surely be removed.

According to the above configuration, an air passage that communicates with the air intake 15, the first air outlet 11, the second air outlet 12, the third air outlet 13 and the fourth air outlet 14 is formed. In this state of assembly, in the vicinity of the first outlet 21, the first air outlet 11 and the third air outlet 13, ion generating electrode sections for generating the minus ions are to be arranged respectively, and in the vicinity of the second outlet 22, the second air outlet 12, the fourth outlet 24 and the fourth air outlet 14, ion generating electrode sections for generating the positive ions are to be arranged respectively. Note that, the aforementioned fan is attached such that its rotation axis is orthogonal to the faces of the air intake 15, the first air outlet 11, the second air outlet 12, the third air outlet 13 and the fourth air outlet 14.

Further, at an inner face of the cover 1 (at a face of the cover 1 on a side facing the intake grill 2), a protruding bar 16 is provided with standing at a position which aligns with the microswitch 35 provided in the main body base 3. When the cover 1 is attached, in other words, when the cover 1 is in a state of being closed (closed state) with respect to the casing 4 (intake grill 2), the protruding bar 16 functions as a pressing section, and presses the microswitch 35 serving as a section to be pressed and thereby the microswitch 35 is turned on. On the other hand, when the cover 1 is detached, in other words, when the cover 1 is in a state of being opened (opened state), the protruding bar 16 is released from the microswitch 35, thus does not press the microswitch 35, and thereby the microswitch 35 is turned off. According to this configuration, by detecting whether the microswitch 35 is being pressed, the opened/closed state of the cover 1 can be detected. The microswitch 35 and the protruding bar 16 become a set of switches as a means for detecting the opened/closed state of the cover 1.

Further, at the rear face side of the air intake 15 of the cover 1, a filter (not depicted) that removes dust included in the air taken into the inside of the ion generating unit 100 is provided.

In the ion generating unit 100 configured as above, when the fan 33 is operated, the air is taken in from the air intake 15. The air taken in passes through the fan 33, flows through the passage constituted of the outlet direction setting member of the intake grill 2, and is blown out from the first air outlet 11, the second air outlet 12, the third air outlet 13 and the fourth air outlet 14. Upon being blown out from the first air outlet 11 and the third air outlet 13, the minus ions generated in the minus ion generating electrode sections of the ion generating element A 31 and the ion generating element B 32 are included in the air, and the air containing the minus ions is sent outside. Further, upon being blown out from the second air outlet 12 and the fourth air outlet 14, the positive ions generated in the positive ion generating electrode sections of the ion generating element A 31 and the ion generating element B 32 are included in the air, and the air containing the positive ions is sent outside. By forming the passage as aforementioned, the air containing the positive ions and the air containing minus ions can be blown out from different air outlets respectively and independently. Thus, the positive ions and the minus ions are prevented from being bonded immediately after their generation, and since the positive ions and the minus ions can be emitted to the outside immediately after their generation, they can be dispersed even to a farther range.

Figure 5:
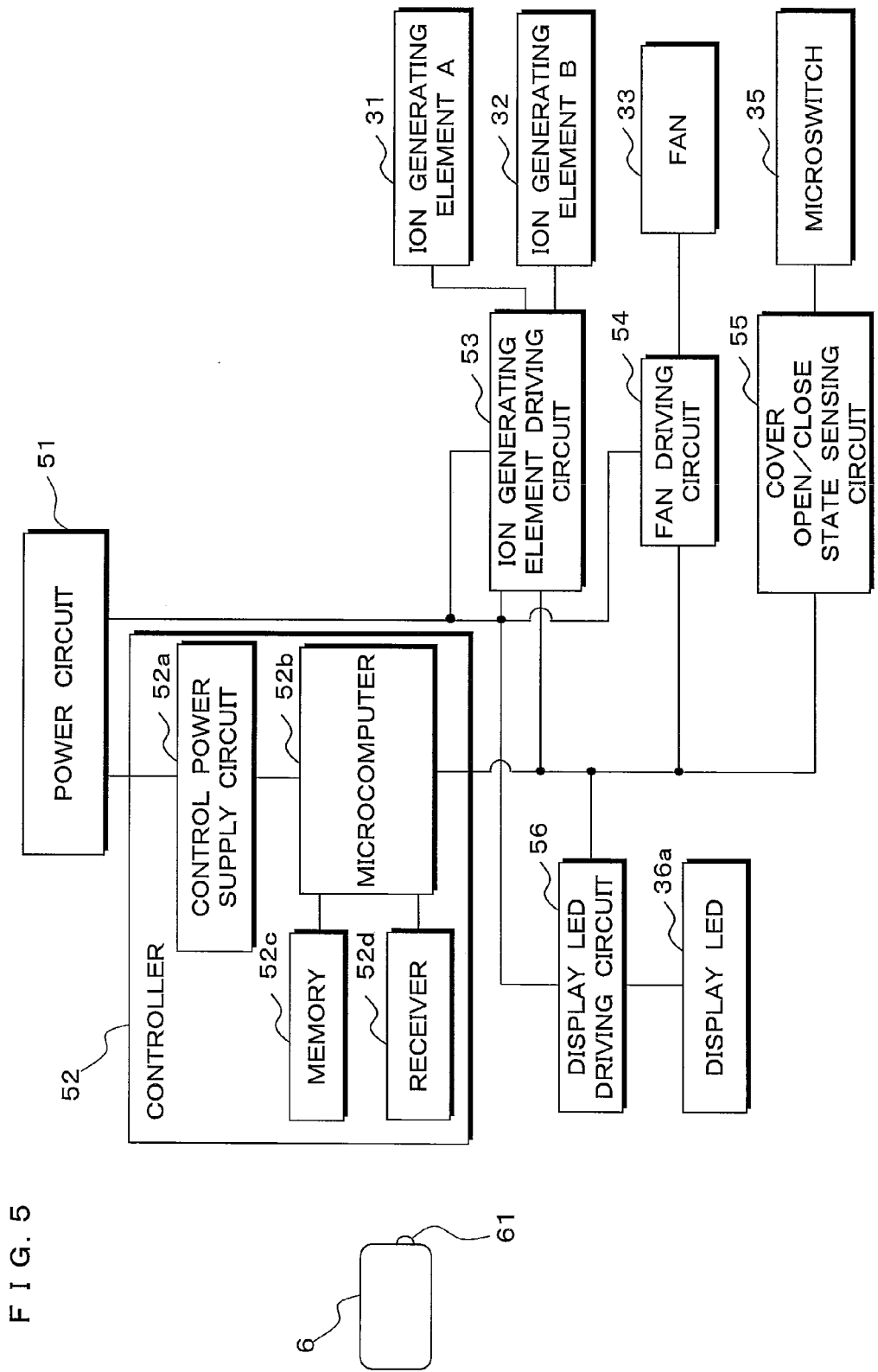
FIG. 5 is a block diagram showing a configuration of a control system of the ion generating unit.

FIG. 5 is a block diagram showing a configuration of a control system of the ion generating unit 100. The electrical circuit substrate 5 of the ion generating unit 100 is provided with a power circuit 51. The power circuit 51 is connected to a utility AC power source via terminal blocks arranged at appropriate positions. The power circuit 51 includes a rectifying circuit that rectifies current supplied from the utility AC power source, a transducer that converts the rectified voltage to a predetermined voltage (33V), and a constant current supply circuit that supplies constant current. In the power circuit 51, a controller 52 that is similarly provided in the electrical circuit substrate 5 is connected thereto, and the power circuit 51 provides power of constant current of 33V to the controller 52.

The controller 52 includes a control power supply circuit 52*a* that decreases the power of 33V to 5V and supplies the same, a microcomputer 52*b* for controlling the ion generating unit 100, a memory 52*c* that stores contents of settings, and a receiver 52*d* that receives infrared lights from a remote controller 6. The control power supply circuit 52*a*, the memory 52*c* and the receiver 52*d* are respectively connected to the microcomputer 52*b*. The control power supply circuit 52*a* supplies the power of 5V to the microcomputer 52*b*. The remote controller 6 includes a power switch that allows operations to turn on or turn off the ion generating unit 100, a switch that allows operations to select a drive mode (high/medium/low) of the ion generating unit 100, and a transmitter 61 that sends infrared signals corresponding to the operations on the switches. Note that, the drive mode is determined according to the amount of ion to be generated.

The microcomputer 52*b* is connected to an ion generating element driving circuit 53, a fan driving circuit 54, a cover open/close state sensing circuit 55 and a display LED driving circuit 56, that are similarly provided in the electrical circuit substrate 5. The cover open/close state sensing circuit 55 provides the microcomputer 52*b* with signals corresponding to the aforesaid output signals of the microswitch 35. The microcomputer 52*b* provides control signals to each of the ion generating element driving circuit 53, the fan driving circuit 54 and the display LED driving circuit 56 in accordance with a program stored in the memory 52*c* and based on the infrared signals from the remote controller 6 received by the receiver 52*d* and the signals from the cover open/close state sensing circuit 55. Power is provided from the power circuit 51 to each of the ion generating element driving circuit 53, the fan driving circuit 54 and the display LED driving circuit 56.

The ion generating element A 31 and the ion generating element B 32 are respectively connected to the ion generating element driving circuit 53, and the ion generating circuit 53 provides the ion generating element A 31 and the ion generating element B 32 with AC high voltages in accordance with the control signals given by the microcomputer 52*b*. The ion generating element A 31 and the ion generating element B 32 generate ions in response to the provided high voltages.

A motor of the fan 33 is connected to the fan driving circuit 54, and the fan driving circuit 54 performs PWM control in accordance with the control signals given by the microcomputer 52*b*, such that the motor of the fan 33 rotates at a predetermined revolution. The fan 33 is rotated by the motor.

Display LEDs 36*a* provided in the display unit 36 are connected to the display LED driving circuit 56, and the display LED driving circuit 56 drives the display LEDs 36*a* in accordance with the control signals given by the microcomputer 52*b*, such that the operational state of the ion generating unit 100 (e.g., a distinction of being driven or stopped, the drive mode, a sign for replacement of the filter, etc.) is indicated.

Figure 6:
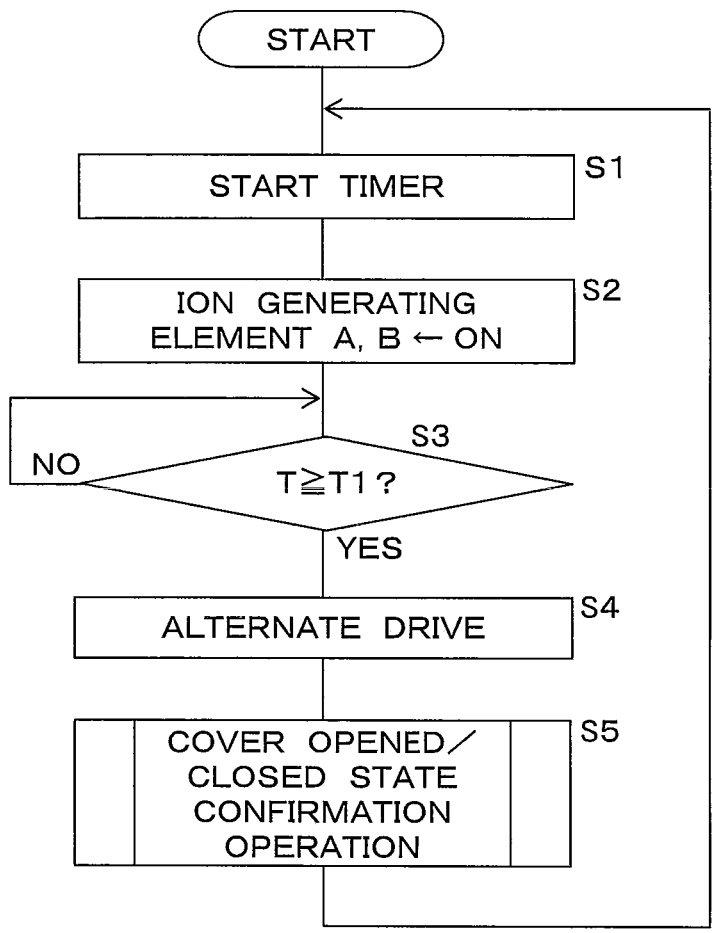
FIG. 6 is a flowchart showing an example of a process procedure of a drive control of an ion generating element A and an ion generating element B, which constitute ion generators.
Figure 7A:
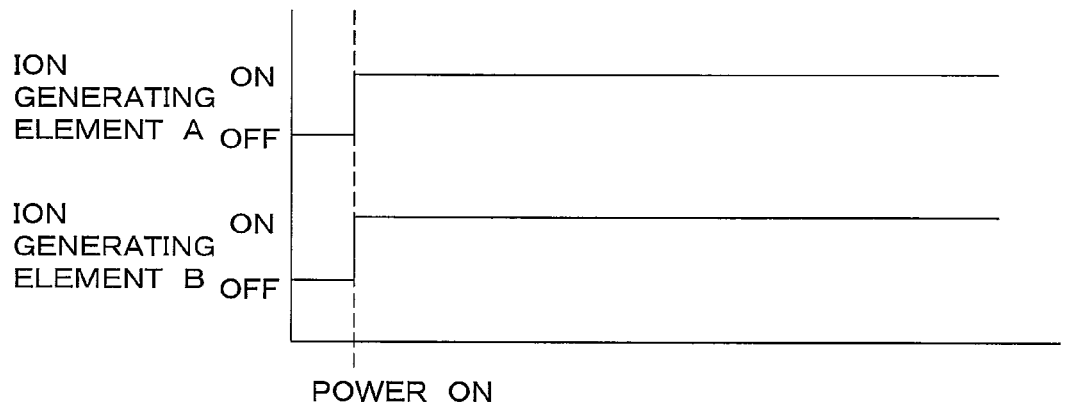
FIG. 7A is a timing chart showing driving states of the ion generating element A and the ion generating element B.
Figure 7B:
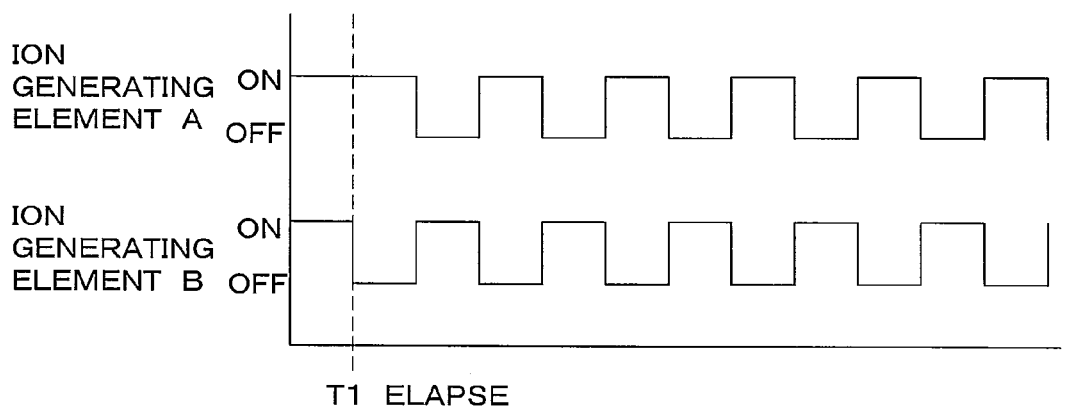
FIG. 7B is the timing chart showing the driving states of the ion generating element A and the ion generating element B.
Figure 7C:
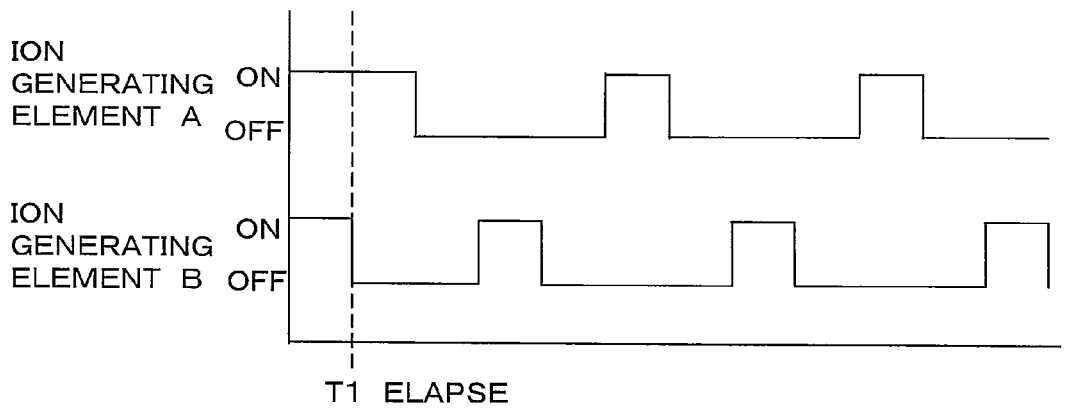
FIG. 7C is the timing chart showing the driving states of the ion generating element A and the ion generating element B.

FIG. 6 is a flowchart showing an example of a process procedure of a drive control of the ion generating element A 31 and the ion generating element B 32, which constitute the ion generators. After the power of the ion generating unit 100 is turned on, the microcomputer 52*b* starts a timer (Step S1), and drives the ion generating element A 31 and the ion generating element B 32 (Step S2). FIGS. 7A to 7C are timing charts showing the driving states (on/off) of the ion generating element A 31 and the ion generating element B 32. FIG. 7A is a timing chart showing a continuous drive in which the ion generating element A 31 and the ion generating element B 32 are driven simultaneously and continuously; FIGS. 7B and 7C are timing charts showing an alternate drive (in-turn drive) in which the ion generating element A 31 and the ion generating element B 32 are driven intermittently, and the driving of the ion generating element A 31 and the driving of the ion generating element B 32 are performed alternately (in turn). In Step S2, as shown in FIG. 7A, the microcomputer 52*b* drives the ion generating element A 31 and the ion generating element B 32 simultaneously and continuously.

Then, a determination is made on whether an elapsed time T since the ion generating element A 31 and the ion generating element B 32 began to be driven exceeds a predetermined time period T1 (Step S3). The elapsed time T is measured by the timer started in Step S1. Note that, the predetermined time period T1 is e.g. an hour, and may appropriately be set in accordance with a volume of the room to be used, a performance to generate ions of the ion generating elements, a number of ion generating elements to be arranged within the room or the like.

In Step S3, in a case where the elapsed time T is determined as exceeding the predetermined time period T1 (Step S3: YES), the microcomputer 52*b* alternately drives (drives in turn) the ion generating element A 31 and the ion generating element B 32 (Step S4); and on the other hand, in a case where the elapsed time T is determined as not exceeding the predetermined time period T1 (Step S3: NO), the microcomputer 52*b* repeats the operation by returning to Step S3. Moreover, the alternate drive is performed e.g. as shown in FIG. 7B. At this occasion, the amount of ions blown out from the ion generating unit 100 is the same amount as when only one of the ion generating element A 31 and the ion generating element B 32 is driven continuously.

Figure 8:
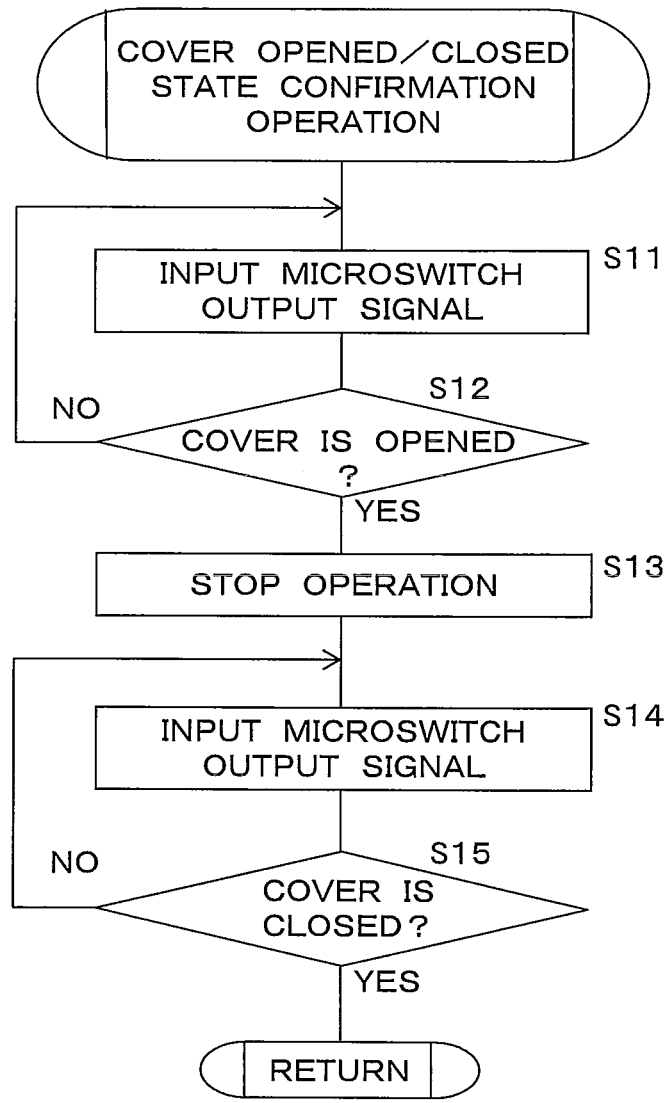
FIG. 8 is a flowchart showing a procedure of a cover opened/closed state confirmation operation.

Next, a cover opened/closed state confirmation operation to confirm the opened/closed state of the cover 1 is performed (Step S5). FIG. 8 is a flowchart showing a procedure of the cover opened/closed state confirmation operation. The microcomputer 52b inputs an output signal from the microswitch 35 (Step S11).

By using the output signal inputted in Step S11, a determination is made on whether or not the cover 1 is in the opened state (Step S12). Note that, as aforementioned, the opening/closing of the cover 1 is detected by the cover open/close state sensing circuit 55 according to the output signal of the microswitch 35 which is turned on/off in response to a detachment/attachment of the cover 1.

In Step S12, in a case where the cover 1 is determined as being in the opened state (Step S12: YES), the microcomputer 52b stops driving the ion generating element A 31 and the ion generating element B 32 and stops the operation of the ion generating unit 100 (Step S13), and proceeds to Step S14. Due to this, in the case where the cover 1 is detached, the operation of the ion generating unit 100 is going to be stopped.

On the other hand, in a case where the cover 1 is determined as not being in the opened state (in the closed state) (Step S12: NO), the alternate drive of the ion generating element A 31 and the ion generating element B 32 is continued, and series of operations are repeated by returning to Step S11.

In Step S14, an output signal from the microswitch 35 is inputted. By using the output signal inputted in Step S14, a determination is made on whether or not the cover 1 is in the closed state (Step S15). In Step S15, in a case where the cover 1 is determined as being in the closed state (Step S15: YES), the process is returned, and series of operations are repeated by returning to Step S1. On the other hand, in a case where the cover 1 is determined as not being in the closed state (in the opened state) (Step S15: NO), the state of the operation being stopped is maintained, and series of operations are repeated by returning to Step S14. The microcomputer 52b terminates the operation of the drive control of the ion generating element A 31 and the ion generating element B 32 when the power of the ion generating unit 100 is cut off.

Note that, the display LEDs 36a provided in the display unit 36 are configured to indicate the operational states of the ion generating unit 100 (e.g., a distinction of the operation being run or stopped, a sign for replacement of the filter, etc.) by the display LED driving circuit 56 that operates in accordance with the control signals provided by the microcomputer 52b.

As aforementioned, the ion generating element A 31 and the ion generating element B 32, which are a plurality of ion generators, are configured to be driven upon start up of the ion generating unit 100 and kept driven continuously for a predetermined time period T1, therefore, the ion concentration in the space can quickly be raised to the predetermined concentration (e.g., a concentration of more than 7,000 ions per unit area of 10 m$^2$) upon start up. Further, after the predetermined time period T1 has elapsed, since it is configured to drive the ion generating element A 31 and the ion generating element B 32 such that their driving time is made substantially equal, only one of the ion generating elements A 31 and B 32 does not run out of its life earlier than the other one; a period during which the predetermined ion concentration can be maintained in the ion generating unit 100 as a whole can be elongated, which consequently brings the elongation of product life of the ion generating unit 100 as a whole. Further, after the predetermined time period T1 has elapsed, it is configured such that the ion generating element A 31 and the ion generating element B 32 are driven intermittently and that the ion generating element A 31 and the ion generating element B 32 are driven alternately. Since it takes some time before the generated ions disappear, so that, by shortening the driving time of the ion generating element A 31 and the ion generating element B 32 while maintaining the predetermined ion concentration, wear of components such as the electric discharge electrodes that constitute the ion generating element A 31 and the ion generating element B 32 can be suppressed, and the elongation of a product life can be achieved.

Figure 9:
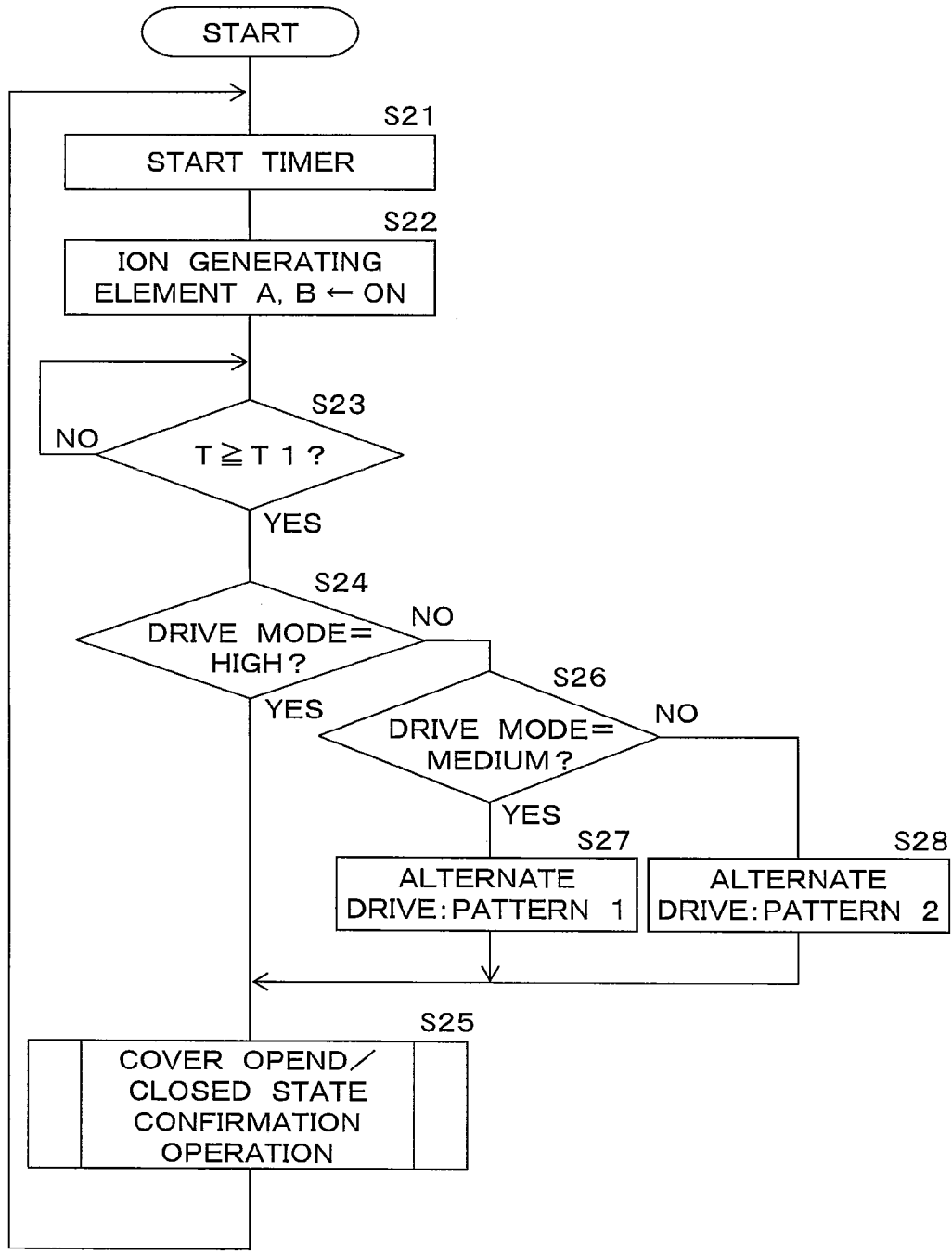
FIG. 9 is a flowchart showing another example of the process procedure of the drive control of the ion generating element A and the ion generating element B.

FIG. 9 is a flowchart showing another example of the process procedure of the drive control of the ion generating element A 31 and the ion generating element B 32. After the power of the ion generating unit 100 is turned on, the microcomputer 52b starts the timer (Step S21), and drives the ion generating element A 31 and the ion generating element B 32 (Step S22). In Step S22, as shown in FIG. 7A, the microcomputer 52b drives the ion generating element A 31 and the ion generating element B 32 simultaneously and continuously.

Next, a determination is made on whether the elapsed time T since the ion generating element A 31 and the ion generating element B 32 began to be driven exceeds the predetermined time period T1 (Step S23). In Step S23, in the case where the elapsed time T is determined as exceeding the predetermined time period T1 (Step S23: YES), the process proceeds to Step S24. On the other hand, in the case where the elapsed time T is determined as not exceeding the predetermined time period T1 (Step S23: NO), the operation is repeated by returning to Step S23.

In Step S24, a determination is made on whether the drive mode set in accordance with the amount of ions to be generated is in a high mode. As aforementioned, the drive mode is selected by using the remote controller 6, and information on the selected drive mode is given to the microcomputer 52b via a transmitter 61 of the remote controller 6 and the receiver 52d of the controller 52. Note that, the high/low of the drive mode correspond to the great/small of the amount of ions to be generated, and the drive mode includes three modes of high/medium/low.

In a case where the drive mode is determined as being in the high mode (Step S24: YES), the continuous drive of the ion generating element A 31 and the ion generating element B 32 is continued, and the process proceeds to Step S25. On the other hand, in a case where the drive mode is determined as not being in the high mode (Step S24: NO), a determination is made on whether the drive mode is in a medium mode (Step S26).

In Step S26, in a case where the drive mode is determined as being in the medium mode (Step S26: YES), the microcomputer 52b alternately drives (drives in turn) the ion generating element A 31 and the ion generating element B 32 in accordance with a pattern 1 (Step S27), and proceeds to Step S25. Note that, the pattern 1 of the alternate drive is performed e.g. as shown in FIG. 7B, and at this occasion, the amount of ions blown out from the ion generating unit 100 is the same amount as when only one of the ion generating element A 31 and the ion generating element B 32 is driven continuously.

On the other hand, in a case where the drive mode is determined as not being in the medium mode (Step S26: NO), that is, in a case where the drive mode is in a low mode, the microcomputer 52b alternately drives (drives in turn) the ion generating element A 31 and the ion generating element B 32 in accordance with a pattern 2 (Step S28), and proceeds to Step S25. Note that, the pattern 2 of the alternate drive is performed e.g. as shown in FIG. 7C, and at this occasion, the amount of ions blown out from the ion generating unit 100 becomes smaller than that of the pattern 1 of the alternate drive.

In Step S25, the cover opened/closed state confirmation operation to confirm the opened/closed state of the cover 1 is performed. The cover opened/closed state confirmation operation is similar to the cover opened/closed state confirmation operation shown in FIG. 8, and the explanation thereof will be omitted. The microcomputer 52b terminates the operation of the drive control of the ion generating element A 31 and the ion generating element B 32 in a case where the power of the ion generating unit 100 is cut off. Note that, in a case where after the predetermined time period T1 has elapsed during which a drive in accordance with a drive mode has been performed and in this case a different drive mode is selected, it is configured to shift to a drive according to the selected drive mode.

Note that, the display LEDs 36a provided in the display unit 36 are configured to indicate the operational states of the ion generating unit 100 (e.g., the distinction of the operation being run or stopped, the drive mode, the sign for replacement of the filter, and or the like) by the display LED driving circuit 56 that operates in accordance with the control signals provided by the microcomputer 52b. For example, two blue LEDs are lit in the case where the drive mode is in the high mode, one blue LED and one green LED are lit in the medium mode, and one blue LED is lit in the low mode.

As aforementioned, the ion generating element A 31 and the ion generating element B 32, which are the plurality of ion generators, are configured to be driven upon start up of the ion generating unit 100 and kept driven continuously for the predetermined time period T1, therefore, the ion concentration in the space can quickly be raised to the predetermined concentration (e.g., the concentration of more than 7,000 ions per unit area of 10 m$^2$) upon start up. Further, after the predetermined time period T1 has elapsed, since it is configured to drive the ion generating element A 31 and the ion generating element B 32 such that their driving time is made substantially equal, only one of the ion generating elements A 31 and B 32 does not run out of its life earlier than the other one; the period during which the predetermined ion concentration can be maintained in the ion generating unit 100 as a whole can be elongated, which consequently brings the elongation of a product life of the ion generating unit 100 as a whole. Further, after the predetermined time period T1 has elapsed, it is configured such that the ion generating element A 31 and the ion generating element B 32 are driven in the continuous drive or alternate drive at the pattern according to the selected drive mode, and thus it becomes capable of increasing and decreasing the amount of ions to be generated by selecting the drive mode, the ion generating element A 31 and the ion generating element B 32 can be driven without any futility while maintaining the ion concentration in the space at the suitable concentration in accordance with the condition of usage of the room or the like, and the elongation of a product life can be achieved.

Note that, although FIG. 7B and FIG. 7C have been presented as the examples of the pattern 1 and pattern 2 of the alternate drive, the present teachings are not limited hereto, so long as the pattern 1 is set to generate greater amount of ions than the pattern 2.

Further, in the above embodiment, although the ion generating element A 31 and the ion generating element B 32 are configured to be driven continuously over the predetermined time period T1 upon start up of the ion generating unit 100, the present teachings are not limited hereto, and may alternatively be configured to be driven alternately. For example, in a case where a starting time at which the room starts to be used is known in advance, the alternate drive may be used in performing the drive at a predetermined time before the starting time.

Figure 10:
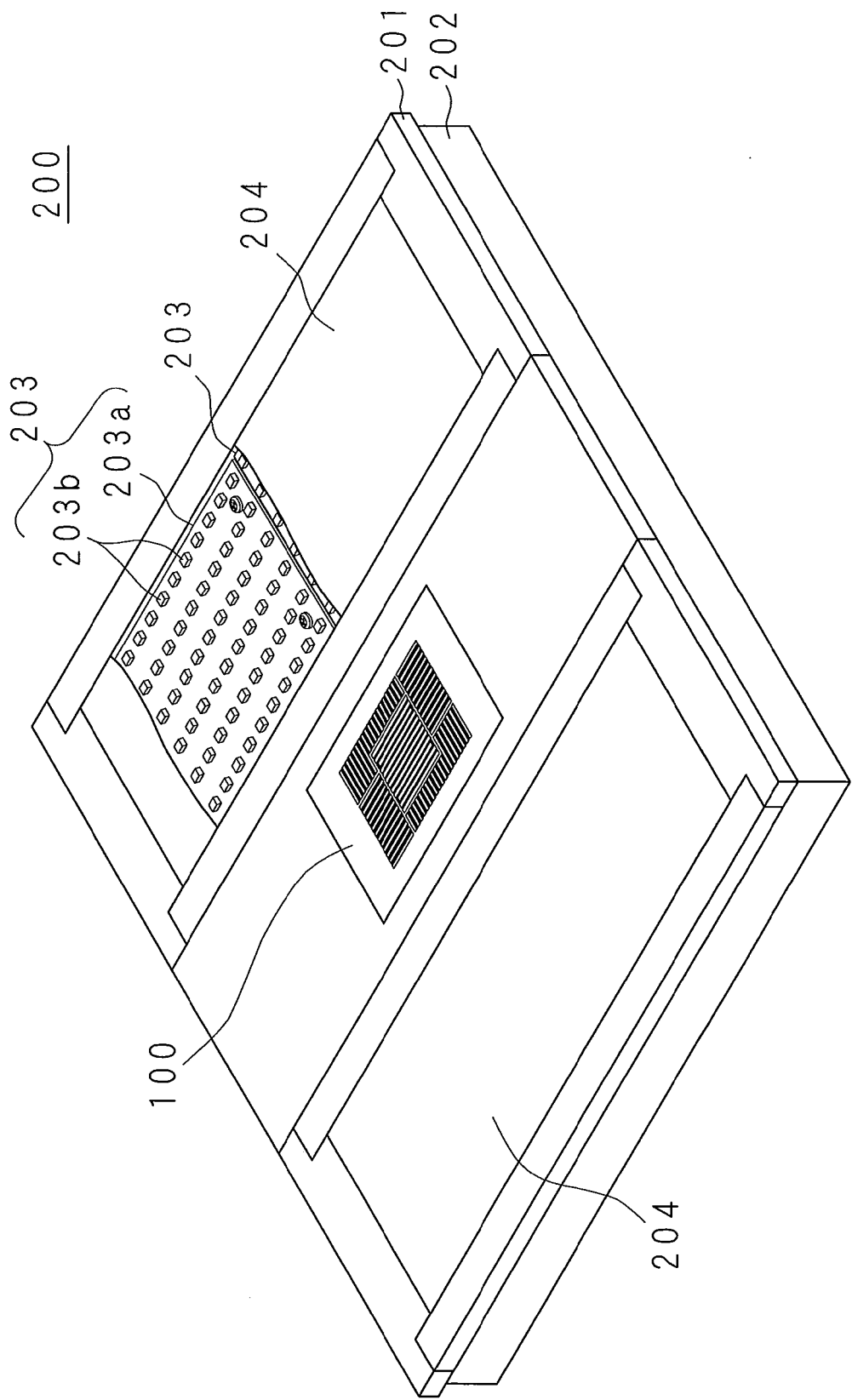
FIG. 10 is an external perspective view of a lighting apparatus including the ion generating unit.

The ion generating unit 100 configured as above may be used by being assembled into a lighting apparatus. FIG. 10 is an external perspective view of a lighting apparatus 200 provided with the ion generating unit 100. The lighting apparatus 200 is a square type lighting apparatus in which a face on a light emitting side has a substantially square shape.

In the figure, 201 is a rectangular cover (frame body) made of resin or metal. A frame (housing) 202 made of metal (e.g. aluminum) which is a housing with one opened face is fitted into this cover 201, and a housing of the lighting apparatus 200 is constituted of the cover 201 and the frame 202. At a center portion of the lighting apparatus 200, the ion generating unit 100 is attached.

On both sides within the lighting apparatus 200 which interpose the ion generating unit 100 therebetween, four lighting LED modules 203, 203 . . . are arranged in two rows by two columns along two edges of the frame 202 facing each other. At an inner face of the cover 201, diffusion plates 204, 204 having rectangular shapes and made of opaque white acrylate resin are each arranged so as to cover the lighting LED modules 203, 203 . . . .

Note that, the lighting LED modules 203, 203 . . . are each configured by an LED substrate 203a which is a rectangular flat plate and a plurality of LEDs 203b, 203b . . . mounted in an equally-spaced matrix on the LED substrate 203a. By arranging a plurality of this type of lighting LED modules 203 adjacent one another, an even emission of light becomes possible. Further, since the light directed from the LEDs 203b is diffused and directed by the diffusion plates 204 that are each arranged at a predetermined interval from a bottom face of the frame 202, a surface emission of light in which a glare as well as an uneven illuminance are reduced is enabled. Accordingly, the diffusion plates 204 function as a light emission surface for an even surface emission of light. The LEDs 203b are high color rendering LEDs in which a blue LED is packaged by sealing with a resin including yellow fluorescent substances and red fluorescent substances. The plurality of LEDs 203b, 203b . . . may be directly attached to the bottom face of the housing 202 without interposing the substrate therebetween.

Figure 11:
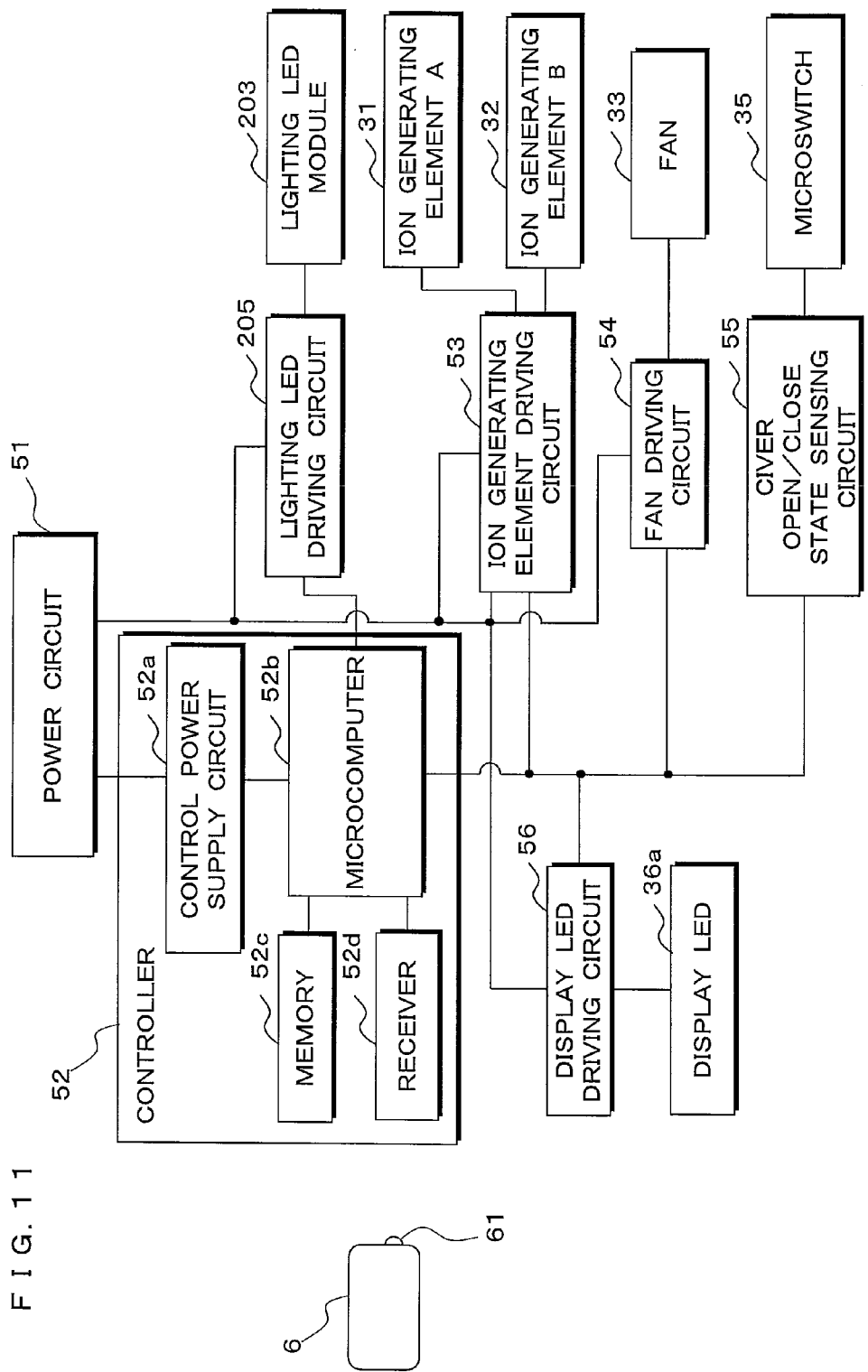
FIG. 11 is a block diagram showing a configuration of a control system of the lighting apparatus including the ion generating unit.

FIG. 11 is a block diagram showing a configuration of a control system of the lighting apparatus 200 provided with the ion generating unit 100. A lighting LED driving circuit 205 is connected to the microcomputer 52b. A power is supplied to the lighting LED driving circuit 205 from the power circuit 51.

The lighting LED modules 203, 203 . . . are connected to the lighting LED driving circuit 205. The lighting LED driving circuit 205 includes respective switching elements therefor, and is configured to open and close the respective switching elements in accordance with the control signals provided by the microcomputer 52b. In response to the opening and closing operations of the switching elements, constant current is supplied to the lighting LED modules 203, 203 . . . , and the lighting LED modules 203, 203 . . . are lit at a predetermined brightness. Remainders of the configuration are similar to the ion generating unit 100 shown in FIG. 5, thus, reference numbers identical to those in FIG. 5 are given to corresponding constituents, and the detailed explanation thereof will be omitted.

Figure 12:
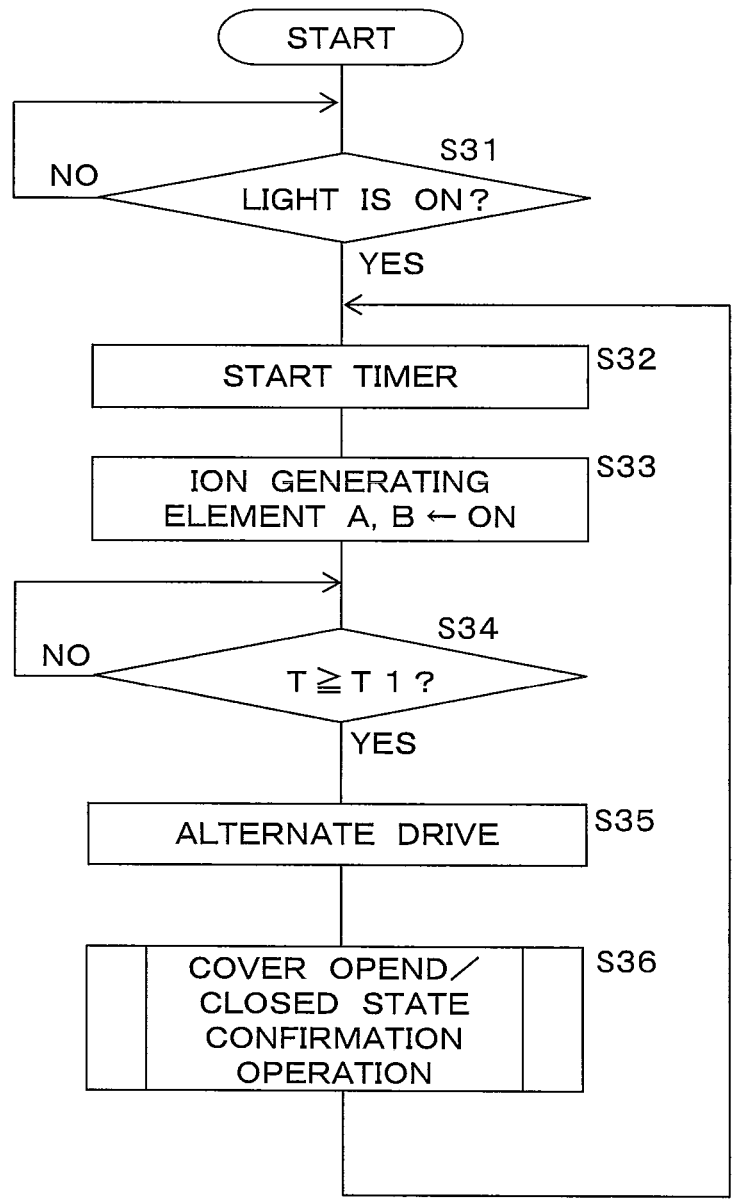
FIG. 12 is a flowchart showing an example of the process procedure of the drive control of the ion generating element A and the ion generating element B in the lighting apparatus including the ion generating unit.

FIG. 12 is a flowchart showing an example of the process procedure of the drive control of the ion generating element A 31 and the ion generating element B 32 in the lighting apparatus 200 provided with the ion generating unit 100. After the power of the ion generating unit 100 is turned on, the microcomputer 52b determines whether or not the light is on (the lighting apparatus 200 is in a lit state) (Step S31). Note that, this determination is performed based on the output signal according to the operation of the power switch provided in the remote controller 6 or the like that is given to the microcomputer 52*b*.

In Step S31, in a case where the light is determined as being on (Step S31: YES), the timer is started (Step S32), the ion generating element A 31 and the ion generating element B 32 are driven (Step S33), and the process proceeds to Step S34. In Step S33, as shown in FIG. 7A, the microcomputer 52*b* simultaneously drives the ion generating element A 31 and the ion generating element B 32, and drives the same continuously. On the other hand, in a case where the light is determined as not being on (Step S31: NO), the operation is repeated by returning to Step S31.

In Step S34, a determination is made on whether the elapsed time T since the ion generating element A 31 and the ion generating element B 32 began to be driven exceeds the predetermined time period T1. In Step S34, in the case where the elapsed time T is determined as exceeding the predetermined time period T1 (Step S34: YES), the microcomputer 52*b* alternately drives (drives in turn) the ion generating element A 31 and the ion generating element B 32 (Step S35). On the other hand, in the case where the elapsed time T is determined as not exceeding the predetermined time period T1 (Step S34: NO), the operation is repeated by returning to Step S34. Note that the alternate drive is performed, e.g., as shown in FIG. 7B.

Next, the cover opened/closed state confirmation operation to confirm the opened/closed state of the cover 1 is performed (Step S36). The cover opened/closed state confirmation operation is similar to the cover opened/closed state confirmation operation shown in FIG. 8, and the explanation thereof will be omitted. After the termination of the cover opened/closed state confirmation operation, series of operations are repeated by returning to Step S32. Note that, the microcomputer 52*b* is configured to pause the series of operations in the case where the light is turned off (the lighting apparatus 200 is in an off state), terminate the operation of the ion generating unit 100, and proceed to Step S31. The microcomputer 52*b* terminates the operation of the drive control of the ion generating element A 31 and the ion generating element B 32 in the case where the power of the ion generating unit 100 is cut off.

As aforementioned, it is configured that the ion generating element A 31 and the ion generating element B 32 which are the plurality of ion generators of the ion generating unit 100 are driven in response to the turn on of the lighting LED modules 203,203 . . . of the lighting apparatus 200; especially in offices and factories, the lighting apparatus is typically turned on when a room is being used, therefore, the ion concentration of the room can quickly be raised to the predetermined concentration when a man uses the room, thereby a clean and comfortable working space or accommodation space can be realized, the ion generating element A 31 and the ion generating element B 32 can be driven without any futility, and the elongation of a product life can be achieved.

Further, as aforementioned, the LEDs are used as the light source. The LEDs have a long product life, and by driving the ion generating element A 31 and the ion generating element B 32 according to the above, the product life of the ion generating element A 31 and the ion generating element B 32 can be elongated. The lighting apparatus is typically arranged at a high place such as a ceiling or the like, and the replacement work is troublesome; however, since the number of replacing the ion generating element A 31 and the ion generating element B 32 or the light source can be reduced, the trouble of the user can be reduced. By suitably setting the drive patterns of the ion generating element A 31 and the ion generating element B 32, the product life of the ion generating element A 31 and the ion generating element B 32 as well as the lighting LED modules 203, 203 . . . can be made to substantially coincide and the replacement can be performed at the same time; thereby, the trouble of the user can further be saved.

Figure 13:
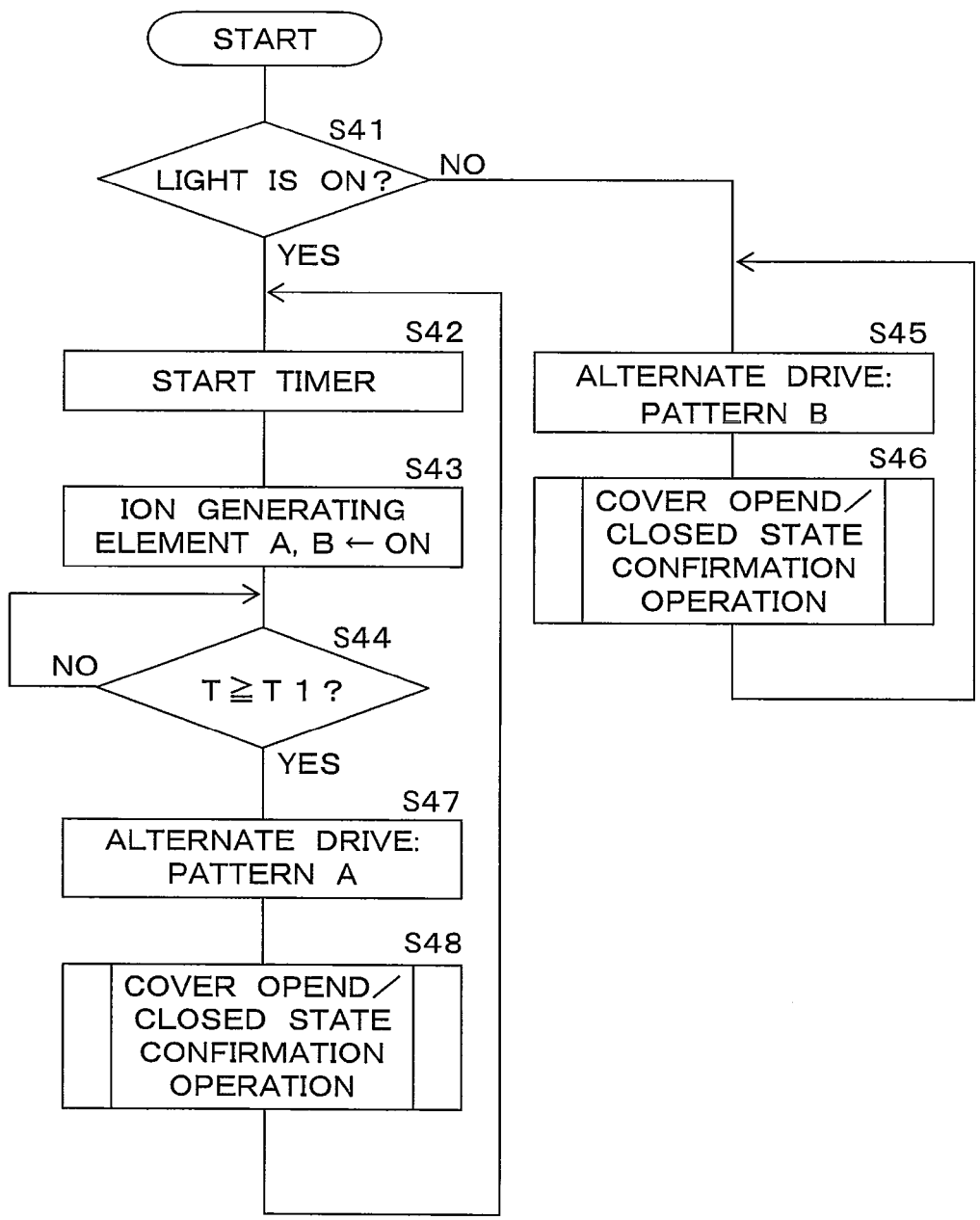
FIG. 13 is a flowchart showing another example of the process procedure of the drive control of the ion generating element A and the ion generating element B in the lighting apparatus including the ion generating unit.

FIG. 13 is a flowchart showing another example of the process procedure of the drive control of the ion generating element A 31 and the ion generating element B 32 in the lighting apparatus 200 provided with the ion generating unit 100. After the power of the ion generating unit 100 is turned on, the microcomputer 52*b* determines whether or not the light is on (the lighting apparatus 200 is in the lit state) (Step S41).

In Step S41, in the case where the light is determined as being on (Step S41: YES), the timer is started (Step S42), the ion generating element A 31 and the ion generating element B 32 are driven (Step S43), and the process proceeds to Step S44. In Step S43, as shown in FIG. 7A, the microcomputer 52*b* simultaneously drives the ion generating element A 31 and the ion generating element B 32, and drives the same continuously.

On the other hand, in the case where the light is determined as not being on (Step S41: NO), the microcomputer 52*b* alternately drives (drives in turn) the ion generating element A 31 and the ion generating element B 32 (Step S45). In Step S45, the microcomputer 52*b* drives the ion generating element A 31 and the ion generating element B 32 e.g. as shown in FIG. 7C. Next, the cover opened/closed state confirmation operation to confirm the opened/closed state of the cover 1 is performed (Step S46). The cover opened/closed state confirmation operation is similar to the cover opened/closed state confirmation operation shown in FIG. 8, and the explanation thereof will be omitted. After the termination of the cover opened/closed state confirmation operation, the series of operations are repeated by returning to Step S45. Note that, the microcomputer 52*b* is configured to pause the series of operations of Steps S45 and S46 in the case where the light is turned on, and to proceed to Step S47.

In Step S44, a determination is made on whether the elapsed time T since the ion generating element A 31 and the ion generating element B 32 began to be driven exceeds the predetermined time period T1. In Step S44, in the case where the elapsed time T is determined as exceeding the predetermined time period T1 (Step S44: YES), the microcomputer 52*b* alternately drives (drives in turn) the ion generating element A 31 and the ion generating element B 32 (Step S47). On the other hand, in the case where the elapsed time T is determined as not exceeding the predetermined time period T1 (Step S44: NO), the operation is repeated by returning to Step S44. In Step S47, the microcomputer 52*b* drives the ion generating element A 31 and the ion generating element B 32 e.g., as shown in FIG. 7B.

Next, the cover opened/closed state confirmation operation to confirm the opened/closed state of the cover 1 is performed (Step S48). The cover opened/closed state confirmation operation is similar to the cover opened/closed state confirmation operation shown in FIG. 8, and the explanation thereof will be omitted. After the termination of the cover opened/closed state confirmation operation, the series of operations are repeated by returning to Step S42. Note that, the microcomputer 52*b* is configured to pause the series of operations and proceed to Step S45 in the case where the light is turned off (the lighting apparatus 200 is in the off state).

In the case where the power of the ion generating unit 100 is cut off, the microcomputer 52*b* terminates the operation of the drive control of the ion generating element A 31 and the ion generating element B 32.

As aforementioned, it is configured to be driven such that the amount of ions to be generated by the ion generating element A 31 and the ion generating element B 32 of the ion generating unit 100 are caused to be great/small in response to a turn-on/turn-off of the lighting LED modules 203,203 . . . of the lighting apparatus 200, respectively. Generally speaking of a turn-on/turn-off of a lighting apparatus, especially in the offices and factories, the lighting apparatus is typically turned on when the room is being used, therefore, the ion concentration of the room can quickly be raised to the predetermined concentration when a man uses the room, thereby a clean and comfortable working space or accommodation space can be realized, the ion generating element A 31 and the ion generating element B 32 can be driven without any futility, and the elongation of a product life can be achieved. Since it is configured such that a small amount of ions are generated even during when the lighting LED modules 203,203 . . . of the lighting apparatus 200 are turned off, the working space or the accommodation space can always be maintained in the clean and comfortable condition.

Note that, in the configuration of the present embodiment, although it is configured such that the amount of ions to be generated by the ion generating element A 31 and the ion generating element B 32 of the ion generating unit 100 is caused to be great/small in response to a turn-on/turn-off of the lighting LED modules 203,203 . . . of the lighting apparatus 200, the present teachings are not limited to this configuration. The amount of ions to be generated by the ion generating unit 100 may be configured to be great/small in response to the high/low of the illuminance of the light of the lighting apparatus 200; further, the turn on/off and the high/low of the illuminance may be combined. For example, the amount of ions to be generated may be changed corresponding to three patterns of: high illuminance/low illuminance/turn off. Due to this, since the high/low of the illuminance of the lighting apparatus typically corresponds to a degree of activeness in human activities, the clean and comfortable working space or accommodation space can be realized, the ion generators can be driven without any futility, and the elongation of a product life can be achieved.

Figure 14:
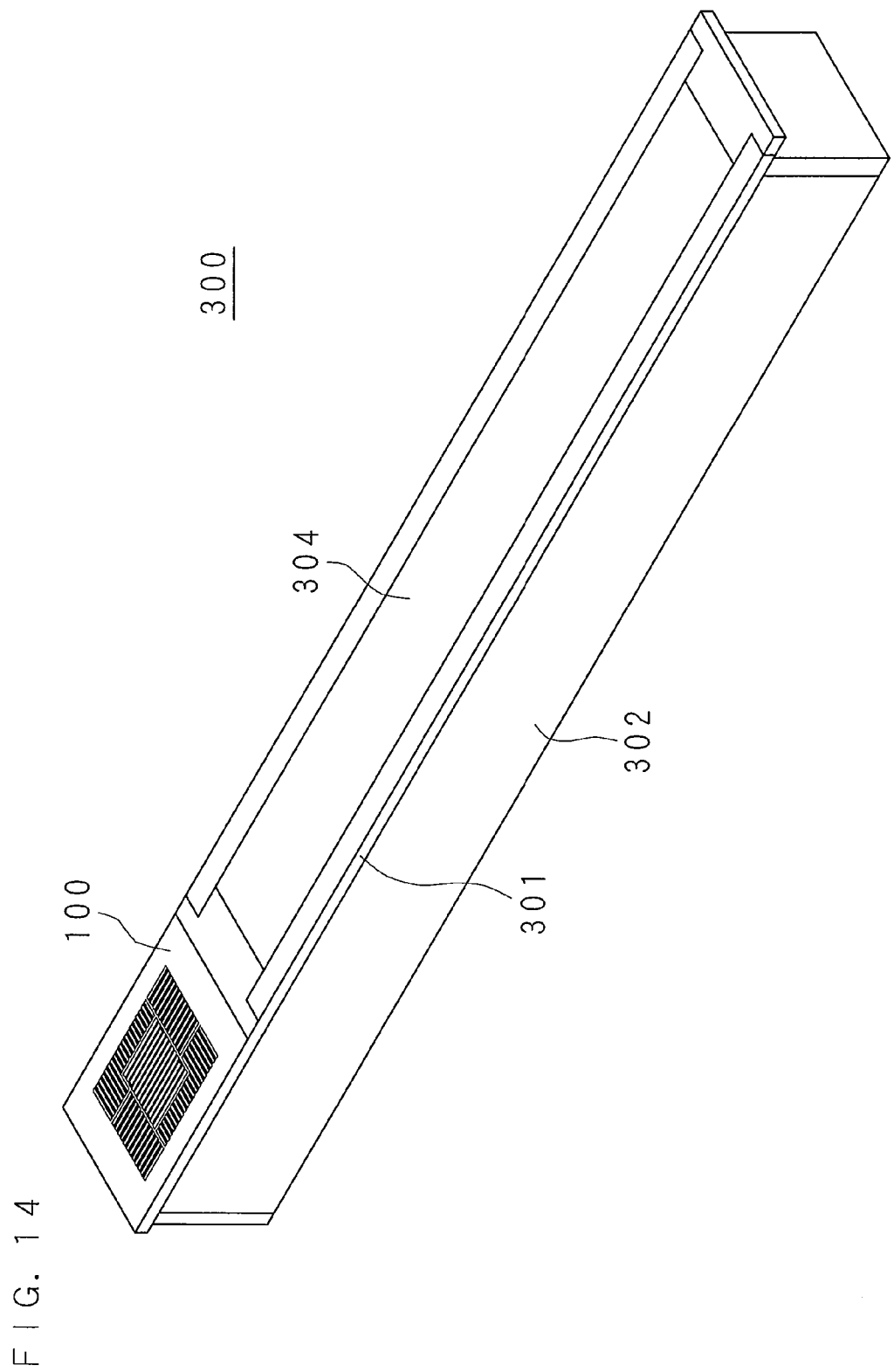
FIG. 14 is an external perspective view of another type of lighting apparatus including an ion generating unit.

FIG. 14 is an external perspective view of another type of lighting apparatus 300 provided with the ion generating unit 100. The lighting apparatus 300 is a straight type lighting apparatus whose face on the light emitting side has a substantially rectangular shape.

In the figure, 301 is a rectangular cover made of resin or metal. A frame 302 made of metal (e.g. aluminum) which is a housing with one opened face is fitted into this cover 301, and a housing of the lighting apparatus 300 is constituted of the cover 301 and the frame 302. At one end portion of the lighting apparatus 300, the ion generating unit 100 is attached.

At an inside of remaining portions of the lighting apparatus 300, a plurality of lighting modules is arranged along a longitudinal direction of the frame 302. At an inner face of the cover 301, diffusion plates 304, 304 having rectangular shapes are each arranged so as to cover the lighting LED modules. As the lighting LED modules, LED modules similar to those of the lighting LED modules 203 used in the lighting apparatus 200 may be used.

In this lighting apparatus 300 also, similar to the lighting apparatus 200, it may be configured to be driven such that the amount of ions to be generated by the ion generating element A 31 and the ion generating element B 32 is caused to be great/small in response to a turn-on/turn-off of the lighting LED modules of the lighting apparatus or the high/low of the illuminance respectively. As a result, a clean and comfortable working space or accommodation space can be realized, the ion generators can be driven without any futility, and the elongation of a product life can be achieved.

Further, similar to the lighting apparatus 200, since the lighting apparatus 300 uses the LEDs as the light source thereof, by suitably setting the drive patterns of the ion generating element A 31 and the ion generating element B 32, the product life of the ion generating element A 31 and the ion generating element B 32 as well as the lighting LED modules can be made to substantially coincide, and the replacement work can be performed at the same time; thereby, the trouble of the user can further be reduced.

Note that, in the lighting apparatus provided with the aforementioned ion generating unit 100, although it is configured such that the drive patterns of the ion generating element A 31 and the ion generating element B 32 of the ion generating unit 100 are determined in response to a turn-on/turn-off of the lighting apparatus being, the present teachings are not limited to this configuration; it may be configured that the drive patterns of the ion generating element A 31 and the ion generating element B 32 are determined in response to the turn on/off of the lighting apparatus and/or high/low of the illuminance thereof. Further, in addition to the turn on/off of the lighting apparatus and/or high/low of the illuminance, the drive patterns of the ion generating element A 31 and the ion generating element B 32 may be determined according to the drive modes (high/medium/low) selected by the remote controller 6. In this case, the alternate drive pattern may appropriately be set so that the amount of ions to be generated is changed according to combinations of the drive modes, the turn on/off of the lighting apparatus and/or high/low of the illuminance.

Further, in the lighting apparatus provided with the aforementioned ion generating unit 100, the ion generating element A 31 and the ion generating element B 32 are driven in connection with the lighting apparatus, the present teachings are not limited to this configuration; it may be configured that the ion generating element A 31 and the ion generating element B 32 are driven in advance. For example, in the case where the starting time at which the room starts to be used is known in advance, the ion generating element A 31 and the ion generating element B 32 may be driven at the predetermined time before the starting time.

Note that, although FIG. 7 has been used to explain the drive patterns of the ion generating element A 31 and the ion generating element B 32, it goes without saying that the present teachings are not limited to this configuration. As an alternate drive pattern, a pattern having a time during which the ion generating element A 31 and the ion generating element B 32 are both not driven is shorter or longer than the pattern shown in FIG. 7C may be employed; and a pattern of the alternate drive having a time during which the drives of the ion generating element A 31 and the ion generating element B 32 are partially overlapped and driven simultaneously may be employed.

Further, in the above embodiments, although the ion generating unit 100 includes the ion generating element A 31 and the ion generating element B 32, the present teachings are not limited to this, and may include three or more ion generating elements. In this case, it may be configured that the plurality of ion generating elements are driven one after another in order; e.g., in the case with three ion generating elements A, B and C, they may be driven one after another in an order of A, B, C, and then A, and so on.

Further, in the above embodiments, the air cleaning unit has been taken as the example of the ion generating unit, however, the present teachings are not limited to this, and may be adapted to other electrical apparatuses that can exhaust air to the outside, e.g., an air conditioning apparatus (air conditioner) or the like.

In the above embodiments, the ion generating unit 100 and the lighting apparatuses 200, 300 provided with the ion generating unit 100 configured such that the ion concentration can quickly be raised to the predetermined concentration upon start up, and the predetermined ion concentration is maintained and the product life is elongated have been described. Accordingly, in a lighting apparatus provided with electric apparatuses such as an ion generating unit, when a need to replace the electric apparatus due to breakage or the like arises, it is configured to be capable of simply replacing the aforesaid electric apparatus exclusively (e.g., the invention of Japanese Patent Application Laid-Open No.2004-146335).

In the lighting apparatus of the aforementioned invention, the minus ion generating apparatus that is the electric apparatus is configured to be capable of being detachably attached to the lighting apparatus main body. However, since it is configured such that the power supply to a lamp which is the light source is stopped when the minus ion generating apparatus is detached from the lighting apparatus main body, when the minus ion generating apparatus is detached from the lighting apparatus main body so as to replace the same, lighting could not be continuously performed by the lamp. Thus, in a case where the time range during which the replacement of the minus ion generating apparatus is night and the place where the lighting apparatus is arranged is dark, there had been a problem that the replacement of the minus ion generating apparatus is difficult. Further, in order for this lighting apparatus to drive the lamp even during the replacement of the minus ion generating apparatus, a connecting cord for supplying power to the lamp needs to be changed to connect to a connecting cord that is connected to a turn-on circuit. Consequently, in dark places as aforementioned, the replacement work of the minus ion generating apparatus had particularly been difficult.

As a lighting apparatus configured such that a replacement work of an electric apparatus can be performed easily, a lighting apparatus provided with an ion generating unit as the electric apparatus will be described as an example with reference to the drawings. The aforementioned ion generating unit is an ion generating unit that generates positive ions and minus ions, and is the aforementioned ion generating unit 100. Hereinbelow, an explanation will be made with the lighting apparatus 200 provided with the ion generating unit 100 as shown in FIG. 10.

Figure 15:
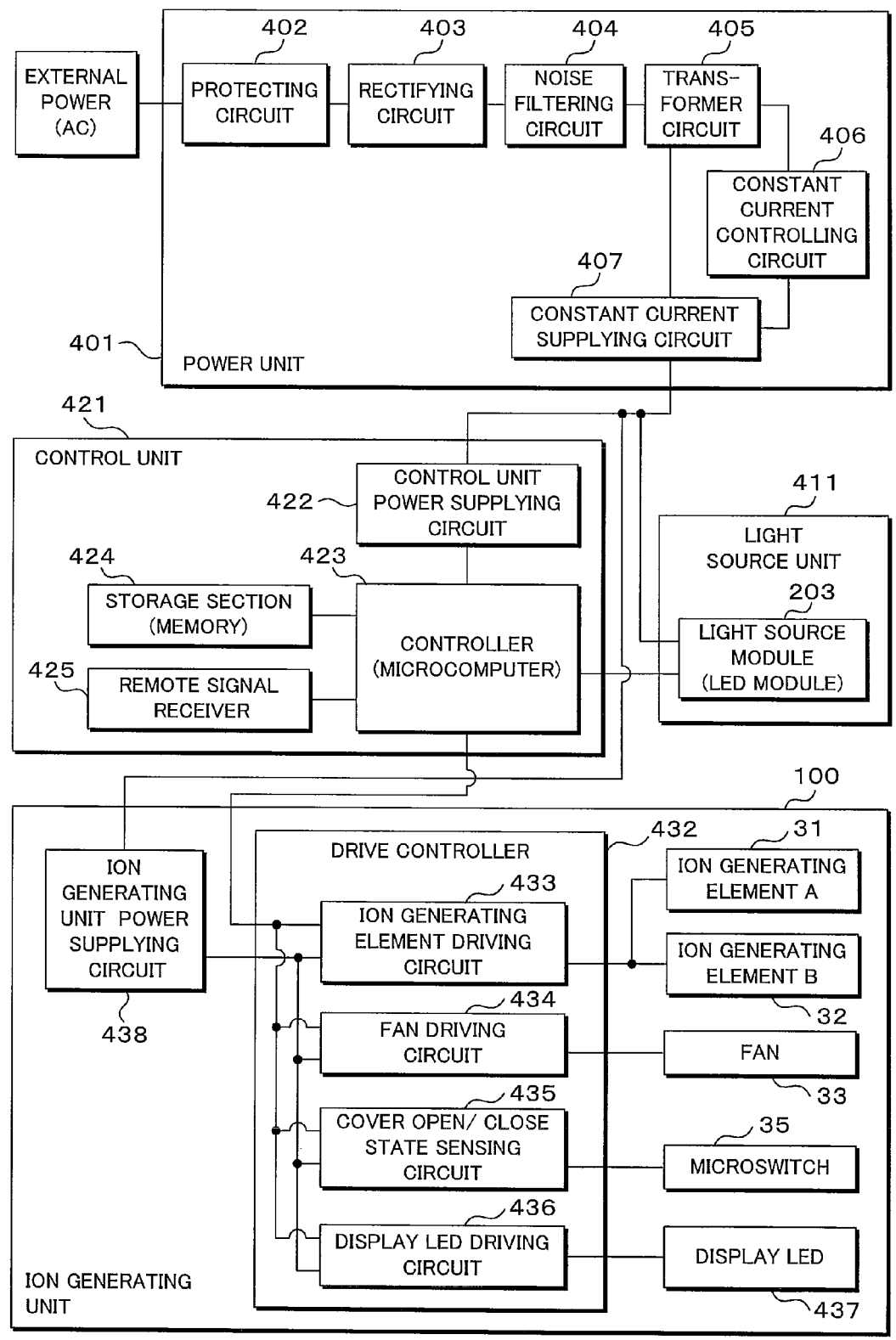
FIG. 15 is a block diagram of a primary part of the lighting apparatus of FIG. 10.

FIG. 15 is a block diagram of a primary part of the lighting apparatus 200 of FIG. 10. Connections and controls of the respective units constituting the lighting apparatus 200 will be explained using FIG. 15.

The lighting apparatus 200 includes a power unit (power circuit) 401 that converts an AC power externally supplied to a constant current and supplies the same to the respective units such as a light source unit 411 including LED modules (lighting LED modules) 203, the light source unit 411 that emits light by receiving the constant current supplied from the power unit 401, an ion generating unit 100 that is driven by receiving the constant current supplied from the power unit 401, and a control unit (controller) 421 that independently controls the light source unit 411 and the ion generating unit 100 by receiving the constant current supplied from the power unit 401.

The power unit 401 is a power unit that converts the external AC power to the constant current power, and is provided with a protecting circuit 402, a rectifying circuit 403 that performs a full-wave rectification on an alternate current, a noise filtering circuit 404 that removes a noise, a transformer circuit 405 that decreases a voltage to a predetermined voltage (33V) for driving the LED modules 203, and the like, a constant current supplying circuit 407 that supplies the constant current to the LED modules 203, and the like, and a constant current controlling circuit 406 that controls the current supplied from the constant current supplying circuit 407 to be a stable constant current.

The light source unit 411 includes a plurality of LED modules 203 as its light source modules. Since the driving voltage of the LED modules 203 is 33V, the constant current supplying circuit 407 is set such that the constant current is a power of 33V.

The control unit 421 is provided with a microcomputer 423 as the controller that controls the light source unit 411 and the ion generating unit 100, a control unit power supplying circuit 422 that decreases the 33V power supplied from the constant current supplying circuit 407 to a driving voltage (5V) of the microcomputer 423, supplies the power to the microcomputer 423 and drives the same, a memory 424 such as EEPROM as a memory referenced by the microcomputer 423, and a remote signal receiver 425 that receives infrared signals such as turn on or off of the power of each unit from an external remote controller, a light modulation of the light source unit 411.

The ion generating unit 100 is provided with an ion generating unit power supplying circuit 438 that decreases the 33V power supplied from the constant current supplying circuit 407 to a predetermined voltage (12V) and supplies power to a drive control circuit 432, and the drive controller 432 that includes an ion generating element driving circuit 433 that drives an ion generating element A 31 and the ion generating element B 32, a fan driving circuit 434 that drives a fan 33, a cover open/close detecting circuit 435 that detects an opened/closed state of a cover 1, and a display LED driving circuit 436 that controls display LEDs 437.

Figure 16:
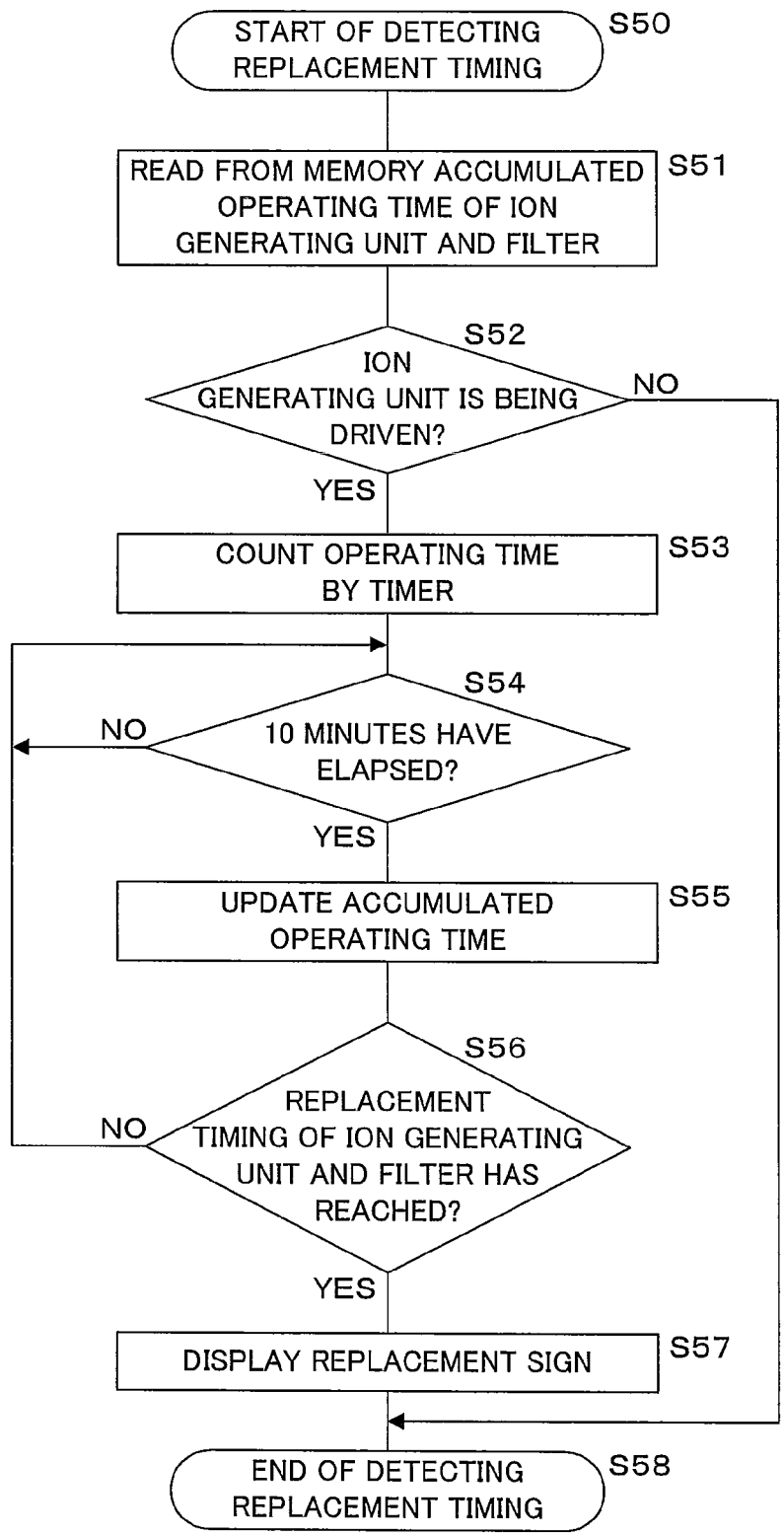
FIG. 16 is a control flowchart for indicating signs for replacement of the ion generating unit and a filter in the lighting apparatus of FIG. 10.
Figure 17:
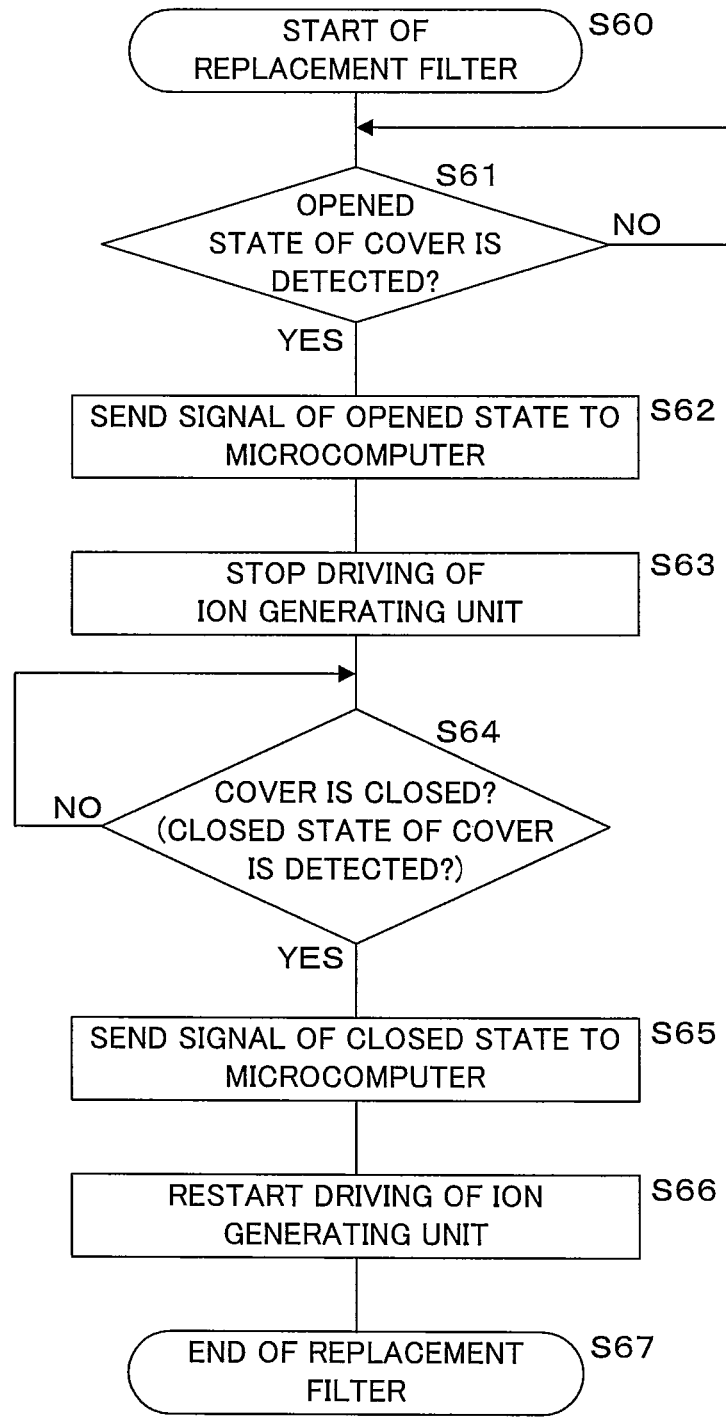
FIG. 17 is a control flowchart upon replacing the filter in the lighting apparatus of FIG. 10.

FIG. 16 is a control flowchart for indicating a sign for replacement of the ion generating unit and the filter in the lighting apparatus of FIG. 10. FIG. 17 is a control flowchart upon replacing the filter in the lighting apparatus of FIG. 10. Firstly, using FIG. 16, the control for indicating the sign for replacement of the ion generating unit 100 and the filter in the lighting apparatus 200 will be explained.

When the power of the lighting apparatus 200 is turned on (S50), firstly, the microcomputer 423 reads respective accumulated operating time of the ion generating unit 100 and the filter that is stored in the memory 424 until a termination of a previous driving (S51).

Next, a determination is made on whether the ion generating unit 100 is currently being driven or not (S52). In a case where the ion generating unit 100 is not being driven, the calculation of operating time of the ion generating unit 100 and the filter will not be necessary, and the control flow for indicating the sign for replacement is terminated (S58).

In a case where the ion generating unit 100 is being driven, the operating time of the ion generating unit 100 and the filter is counted by using a timer installed in the microcomputer 423 (S53). The counting of the operating time is performed on the driving time of the ion generating unit 100 for every predetermined time interval (in a unit of 10 minutes). Specifically, a determination is made on whether the driving of the ion generating unit 100 has been continued for 10 minutes (S54), and every time 10 minutes has elapsed, the accumulated operating time of the ion generating unit 100 and filter that is stored in the memory 424 is updated by incrementing by the unit of 10 minutes (S55). Note that, in a case where the driving is not continued for 10 minutes due to a turn-on/turn-off of the power of the ion generating unit 100, the accumulated operating time in the memory 424 is not updated.

Next, a determination is made on whether the accumulated operating time of the ion generating unit 100 and filter has reached a predetermined replacement timing that is set in advance and stored in the memory 424 (S56). In a case where the replacement timing has not been reached, the counting of the operating time is continued according to the aforementioned control flow so long as the driving of the ion generating unit 100 is continued (S54). Further, in a case where the replacement timing has been reached, a warning is addressed to a user by indicating the replacement sign in the display unit 36 (S57). According to the above, the control flow of the replacement time detection of the ion generating unit 100 and filter is terminated (S58).

Moreover, the replacement timing of the ion generating unit 100 stored in the memory 424 is 20,000 hours, and the replacement timing of the filter is 1500 hours. If the ion generating unit 100 is continuously used even after having reached its replacement timing, a situation in which the positive ions and minus ions are not emitted from the ion generating unit 100 (the ion generating element A 31 and the ion generating element B 32) would happen, and the air cleaning function may not be exhibited sufficiently in such a case.

Further, if the replacement of the filter is not performed, the filter may be clogged with dust, etc., and air may not be sufficiently taken into the ion generating unit 100, causing a reduction in the amount of air containing ions that is blown outward. Therefore, the function of the ion generating unit 100 to diffuse the ion-containing air may be degraded.

According to the control as described in the control flow, the replacement timings can surely be visually presented to the user by the indication of the replacement signs in the display unit 36 to warn the user, the degradation in the function of the ion generating unit 100 as aforementioned can be prevented.

Next, using FIG. 17, a control of the ion generating unit 100 upon replacing the filter will be explained. Firstly, a filter replacement work is started (S60), and when the cover 1 is opened to replace the filter, the cover open/close detecting circuit 435 of the ion generating unit 100 detects the opened state of the cover 1 from a condition of pressure on the microswitch 35 (S61). In the case where the opened state of the cover 1 is detected, a signal indicating the opened state is sent to the microcomputer 423 (S62), and the microcomputer 423 controls the ion generating unit 100 and stops the driving thereof (S63). More specifically, the microcomputer 423 sends signals to stop the driving of the ion generating element A 31, the ion generating element B 32 and the fan 33 to the ion generating element driving circuit 433 and the fan driving circuit 434, and the respective driving circuits stop the power supply, to stop the driving. Since the driving of the ion generating unit 100 is stopped, the filter can safely be replaced.

Thereafter, when the cover 1 is closed and the protruding bar 16 of the cover 1 returns to its state of pressing the microswitch 35 again, the cover open/close detecting circuit 435 detects the closed state of the cover 1 (S64). In the case where the closed state of the cover 1 is detected, a signal indicating the closed state is sent to the microcomputer 423 (S65), and the driving of the ion generating unit 100 is restarted automatically (S66).

The aforementioned control is performed upon the replacement of the filter, and a safe filter replacement becomes possible (S67). Further, during the filter replacement, the driving of the ion generating unit 100 (the ion generating element A 31 and the ion generating element B 32) is stopped, but power is continuously supplied to the light source unit 411 of the lighting apparatus 200, and the light emission is continuously performed by driving the light source unit 411. Consequently, the filter can be replaced under the light emission, and thus the filter replacement can easily be performed.

Further, the lighting apparatus 200 is configured such that power is independently supplied to the light source unit 411 and the ion generating unit 100, thus even in the case of replacing the ion generating unit 100 itself, the power can continuously be supplied to the light source unit 411, and the replacement of the ion generating unit 100 itself can also be performed under the light emission thereof.

FIG. 18 is a table explaining the lighting states of the display LEDs in the display unit for displaying the indication of operational states of the ion generating unit and the indication of the replacement timings of the filter and the ion generating unit of FIG. 1. For each of the operational states of the ion generating unit 100 listed in the first row of the table, lighting states of a plurality of display LEDs 437 are shown. Note that the display LEDs 437 are provided in the display unit 36 shown in FIG. 2, include a first blue LED, second blue LED, red LED and green LED, and change the color in accordance with the operational states of the ion generating unit 100. Further, the replacement timings of the ion generating unit 100 and the filter are warned to the user by displaying the same by lighting the display LEDs 437.

The ion generating unit 100 includes a plurality of fan driving modes (high rotation mode, medium rotation mode, low rotation mode) having the different number of rotation of the fan 33, and that can be selected by the user by a remote controller or the like. By changing the number of rotation of the fan 33, the ion concentration of the room can be adjusted, and when a stronger air cleaning function within the room is desired, the high rotation mode can be set, and by increasing the number of rotation of the fan by driving the ion generating unit, the ion concentration of the room can be increased so as to strengthen the air cleaning function. Note that, the low rotation mode is a fan driving mode with the smallest number of rotation of the fan, and its air cleaning function is the smallest among the three fan driving modes. Further, the medium rotation mode is an intermediate level between the high rotation mode and the low rotation mode.

Further, the display unit 36 lights the plurality of display LEDs 437 by combining them so that a different color is shown for each of the plurality of fan driving modes. The control of the lighting of the display LEDs 437 is performed by the display LED driving circuit 436 in accordance with a signal that regards the fan driving modes and is sent to the display LED driving circuit 436 from the microcomputer 423.

Note that, as shown in FIG. 18, in a case of the high rotation mode, the first blue LED and second blue LED are lit, in a case of the medium rotation mode, the second blue LED and green LED are lit, and in a case of the low rotation mode, the second blue LED is lit. All of the above are in different colors because, since the ions emitted within the room cannot be seen, it is difficult for the user to determine in which fan driving mode the ion generating unit is being driven.

In the case of indicating the replacement sign of the filter replacement timing, the red LED may be lit, and in the case of indicating the replacement sign of the ion generating unit replacement timing, the second blue LED and green LED may be blinked.

As mentioned above, since the user can visually recognize the replacement timings, the continuous usage of the ion generating unit 100 in the state where a function thereof is degraded can be prevented.

Note that, the combinations of the display LEDs 437 for indicating the operational states of the aforementioned ion generating unit 100 and indicating the replacement timings of the filter and ion generating unit 100 are mere examples. Further, as a configuration to change the colors of the LED modules 203 or that of the LEDs 203a, which are parts of the LED modules 203, the LEDs 203a of the light source unit 411 may be used as the display LEDs. Since the display LEDs do not need to be additionally provided, the cost of the lighting apparatus can be decreased.

Next, a control to reset the lighting display of the display LEDs 437 indicating the replacement timings of the ion generating unit 100 and filter will be explained. The indication of the replacement timing of the filter is continued by lighting the red LED even when the ion generating unit 100 is stopped, and the indication of the replacement timing of the ion generating unit 100 is carried out by blinking the second blue LED and green LED, and thus has a possibility that such may bother the user. Therefore, the lighting apparatus 200 includes the control to reset the lighting display of the signs of replacement for each of the ion generating unit 100 and filter.

Figure 19:
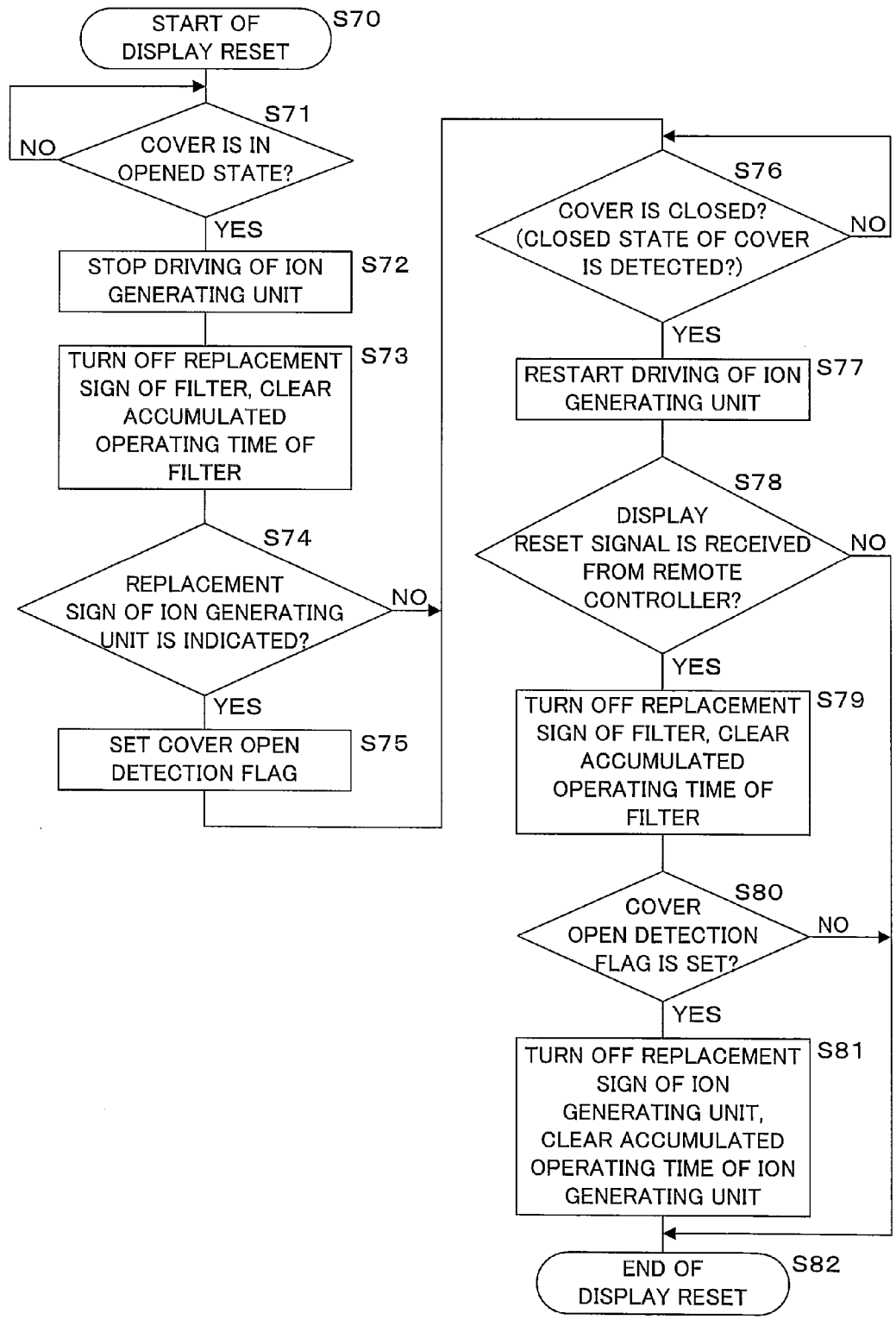
FIG. 19 is a control flowchart for resetting lighting display of the display LEDs that display the replacement timings of the ion generating unit and filter of FIG. 1.

FIG. 19 is a control flowchart for resetting the lighting display of the display LEDs that display the replacement timings of the ion generating unit and the filter of FIG. 1. As shown in FIG. 19, in a case of performing a reset of the lighting display of the display LEDs 437 indicating the replacement timings of the ion generating unit 100 and the filter (S70), firstly, the cover 1 arranged on the front face side of the ion generating unit 100 needs to be detached. When the cover open/close detecting circuit 435 detects that the cover 1 is detached and is in the opened state (S71), the ion generating unit 100 is controlled to stop its driving, and the driving of the ion generating unit 100 is stopped thereby (S72). Note that the detection of the opened state of the cover 1 is performed by detecting the condition of pressure on the microswitch 35 by the cover open/close detecting circuit 435. Once the cover 1 is opened, the display LEDs are turned off when the replacement sign of the filter is displayed, and the accumulated operating time of the filter is cleared (S73).

Next, a determination is made on whether the sign indicated in the display unit 36 is the sign for ion generating unit replacement or not (S74). In a case where it is the sign for ion generating unit replacement, a cover open detection flag is set in the memory 424 (S75), and in a case where it is not the sign for ion generating unit replacement, the cover open detection flag is not set.

Further, when the cover 1 is closed and the cover open/close detecting circuit 435 detects the cover closed state (S76), the driving of the ion generating unit 100 is restarted (S77). Further, a determination is made on whether a display reset signal has been received from an external remote controller or not (S78). In a case where there is no display reset signal, the user does not want to perform a display reset, so that the display of the signs of replacement is continuingly performed (S82).

In a case where there is a receipt of the display reset signal, the display of the replacement sign of the filter is turned off, and the accumulated operating time of the filter stored in the memory 424 is cleared (S79). Further, in a case where the cover open detection flag is set in the memory 424 (S80), the display of the replacement sign of the ion generating unit 100 is turned off, and the accumulated operating time of the ion generating unit stored in the memory 424 is cleared (S81). Thereafter, the control is terminated (S82).

According to the above control, the display of the replacement sign of the filter is reset in either of the cases in which the cover 1 is once opened or the display reset signal from the remote controller is received, however, the display of the replacement sign of the ion generating unit 100 is reset only in the case where the cover 1 is opened or closed and the display reset signal from the remote controller is received. That is, compared with the indication reset of the replacement sign of the filter, the indication reset of the replacement sign of the ion generating unit 100 has greater number of conditions set thereto.

As aforementioned, the lighting apparatus 200 provided with the ion generating unit 100 as shown in FIG. 10 has been explained as an example, a similar configuration can be applied to the lighting apparatus 300 provided with the ion generating unit 100 as shown in FIG. 14. In the lighting apparatus 300 also, similar controls as the lighting apparatus 200 are performed, thus, even if the driving of the ion generating unit 100 shifts to the state of being stopped by detaching the ion generating unit 100 for replacement thereof or opening the cover 1 for the filter replacement, the light emission can continuously be performed by providing power to the light source unit 411. Consequently, the replacement of the ion generating unit 100, or the like can easily be performed under the light emission.

In the above description, as a state in which the ion generating unit is not driven, the occasions of replacing the ion generating unit or the like have been explained as the examples, however, since the electrical apparatuses and the light source are capable of being supplied with power via different lines, the light emission can be continued by supplying power only to the light source even in the state where the ion generating unit 100 is shifted to the state of being stopped with its power turned off. Thus, the user can voluntarily select to turn on or off the power of the ion generating unit 100 during the light emission.

Further, in the above description of the embodiments, the ion generating unit (ion generating apparatus) has been shown as the example of the electric apparatus to be attached to the lighting apparatus, however, the present teachings are not limited hereto. For example, other electric apparatuses such as an air conditioning apparatus may be employed.

Further, in the above description of the embodiments, LEDs are used as the light source, however, the present teachings are not limited hereto, and other light sources such as fluorescents or EL (Electro-Luminescence) may be employed. Further, as the LEDs, high color rendering LEDs are used, however, phosphor-based white LEDs constituted of blue LEDs and yellow phosphor substances may be employed; and yet further, packaged LEDs constituted of red LEDs, green LEDs and blue LEDs may be employed.

It goes without saying that the present invention can further be implemented in embodiments modified in various aspects within the scope of matters described in the Claims.

As this invention may be embodied in several forms without departing from the spirit of essential characteristics thereof, the present embodiments are therefore illustrative and not restrictive, since the scope of the invention is. defined by the appended claims rather than by the description preceding them, and all changes that fall within metes and bounds of the claims, or equivalence of such metes and bounds thereof are therefore intended to be embraced by the claims.

The invention claimed is:

1. An ion generating unit comprising:
   a plurality of ion generators configured to generate ions; and
   a controller configured to control drive of the plurality of ion generators,
   wherein upon start up of the controller, the controller drives all the plurality of ion generators, and after a predetermined time period has elapsed, the controller controls one of the plurality of ion generators to be driven such that a driving time of the plurality of ion generators is substantially equalized.

2. The ion generating unit according to claim 1,
wherein the controller controls to drive the plurality of ion generators one after another in order such that the driving time of the plurality of ion generators is substantially equalized.

3. The ion generating unit according to claim 1,
wherein the controller controls to drive the plurality of ion generators one after another in order by driving respective ones of the plurality of ion generators intermittently.

4. The ion generating unit according to claim 1,
wherein the controller is configured so as to selectively drive the plurality of ion generators continuously.

5. A lighting apparatus comprising:
a light source; and
an ion generating unit according to claim 1.

6. The lighting apparatus according to claim 5,
wherein the light source is an LED.

7. A lighting apparatus comprising:
a light source; and
an ion generating unit according to claim 1,
wherein the controller is configured to drive the plurality of ion generators in response to a turn on of the light source.

8. A lighting apparatus comprising:
a light source; and
an ion generating unit according to claim 1,
wherein the controller is configured to drive the plurality of ion generators such that an amount of generated ion becomes large/small in response to a turn-on/turn-off of the light source and/or high/low of illuminance thereof.

9. An ion generating unit comprising:
a plurality of ion generators configured to generate ions; and
a controller configured to control drive of the plurality of ion generators,
wherein the controller selects and controls one of a first drive for driving all the plurality of ion generators, and a second drive for driving one of the plurality of ion generators such that a driving time of the plurality of ion generators is substantially equalized.

10. The ion generating unit according to claim 9,
wherein the controller controls to drive the plurality of ion generators one after another in order such that the driving time of the plurality of ion generators is substantially equalized.

11. The ion generating unit according to claim 9,
wherein the controller controls to drive the plurality of ion generators one after another in order by driving respective ones of the plurality of ion generators intermittently.

12. A lighting apparatus comprising:
a light source; and
an ion generating unit according to claim 9.

13. The lighting apparatus according to claim 12,
wherein the light source is an LED.

14. A lighting apparatus comprising:
a light source; and
an ion generating unit according to claim 9,
wherein the controller is configured to drive the plurality of ion generators in response to a turn on of the light source.

15. A lighting apparatus comprising:
a light source; and
an ion generating unit according to claim 9,
wherein the controller is configured to drive the plurality of ion generators such that an amount of generated ion becomes large/small in response to a turn-on/turn-off of the light source and/or high/low of illuminance thereof.

\* \* \* \* \*